(12) United States Patent
Gleicher et al.

(10) Patent No.: US 9,157,117 B2
(45) Date of Patent: *Oct. 13, 2015

(54) SCREENING OF OOCYTE DONOR CANDIDATES BASED ON THE FMR1 GENE

(71) Applicants: Norbert Gleicher, New York City, NY (US); David H Barad, Closter, NJ (US)

(72) Inventors: Norbert Gleicher, New York City, NY (US); David H Barad, Closter, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 14/271,607

(22) Filed: May 7, 2014

(65) Prior Publication Data

US 2014/0243585 A1 Aug. 28, 2014

Related U.S. Application Data

(60) Continuation-in-part of application No. 14/220,919, filed on Mar. 20, 2014, which is a continuation-in-part of application No. 14/101,646, filed on Dec. 10, 2013, which is a division of application No. 13/612,566, filed on Sep. 12, 2012, now Pat. No. 8,629,120, which is a continuation-in-part of application No. 13/360,349, filed on Jan. 27, 2012, which is a continuation-in-part of application No. 13/043,199, filed on Mar. 8, 2011, which is a continuation-in-part of application No. 12/508,295, filed on Jul. 23, 2009, now abandoned.

(51) Int. Cl.
| | |
|---|---|
| *C12Q 1/68* | (2006.01) |
| *C07H 21/02* | (2006.01) |
| *C07H 21/04* | (2006.01) |
| *A61B 17/435* | (2006.01) |

(52) U.S. Cl.
CPC ............ *C12Q 1/6881* (2013.01); *A61B 17/435* (2013.01); *C12Q 1/6883* (2013.01); *C12Q 2600/156* (2013.01)

(58) Field of Classification Search
CPC ..... A61K 48/00; C12N 15/113; C12Q 1/6883
See application file for complete search history.

(56) References Cited

PUBLICATIONS

Gleicher N, Weghofer A, Barad DH. Ovarian reserve determinations suggest new function of FMR1 (fragile X gene) in regulating ovarian ageing. Reprod Biomed Online. 2010;20:768-75.
Gleicher N, Weghofer A, Kim A, Barad DH. The impact in older women of ovarian FMR1 genotypes and sub-genotypes on ovarian reserve. PloS one 2012;7:e33638.
Gleicher N, Kim A, Barad DH, Shohat-Tal A, Lazzaroni E, Michaeli T, Lee HJ, Kushnir VA, Weghofer A. FMR1-dependent variability of ovarian aging patterns is already apparent in young oocyte donors. Reprod Biol Endocrinol. 2013;11:80.
Gleicher N, Kim A, Weghofer A, Barad DH. Differences in ovarian aging patterns between races are associated with ovarian genotypes and sub-genotypes of the FMR1 gene. Reprod Biol Endocrinol. 2012;10:77.
Gleicher N, Weghofer A, Lee IH, Barad DH. Association of FMR1 genotypes with in vitro fertilization (IVF) outcomes based on ethnicity/race. PloS one 2011;6:e18781.
Gleicher N, Weghofer A, Lee IH, Barad DH. FMR1 genotype with autoimmunity-associated polycystic ovary-like phenotype and decreased pregnancy chance. PloS one 2010;5:e15303.
Sen A, Kushnir VA, Barad DH, Gleicher N. Endocrine autoimmune diseases and female infertility. Nat Rev Endocrinol. Jan. 2014;10(1):37-50.
Gleicher N, Barad DH. Dehydroepiandrosterone (DHEA) supplementation in diminished ovarian reserve (DOR). Reprod Biol Endocrinol. 2011;9:67.
Gleicher N, Weghofer A, Barad DH. Effects of race/ethnicity on triple CGG counts in the FMR1 gene in infertile women and egg donors. Reproductive biomedicine online 2010;20:485-91.
Fragouli E, Wells D. Aneuploidy screening for embryo selection. Semin Reprod Med. 2012;30:289-301.
Goto S, Kadowaki T, Tanaka S, Hashimoto H, Kokeguchi S, Shiotani M. Prediction of pregnancy rate by blastocyst morphological score and age, based on 1,488 single frozen-thawed blastocyst transfer cycles. Fertil Steril. 2011;95:948-52.
Gleicher N, Weghofer A, Barad DH. Cutting edge assessment of the impact of autoimmunity on female reproductive success. J Autoimmun. 2012;38:J74-80.
Setti AS, Figueira RC, Braga DP, Colturato SS, Iaconelli A, Jr., Borges E, Jr. Relationship between oocyte abnormal morphology and intracytoplasmic sperm injection outcomes: a meta-analysis. Eur J Obstet Gynecol Reprod Biol. 2011;159:364-70.
Alfarawati S, Fragouli E, Coils P, Stevens J, Gutiérrez-Mateo C, Schoolcraft WB, Katz-Jaffe MG, Wells D. The relationship between blastocyst morphology, chromosomal abnormality, and embryo gender. Fertil Steril. 2011;95:520-4.
Gleicher N, Barad DH. A review of, and commentary on, the ongoing second clinical introduction of preimplantation genetic screening (PGS) to routine IVF practice. J Assist Reprod Genet. 2012;29:1159-66.
Gleicher N, Kim A, Weghofer A, Kushnir VA, Shohat-Tal A, Lazzaroni E, Lee HJ, Barad DH. Hypoandrogenism in association with diminished functional ovarian reserve. Hum Reprod. 2013;28:1084-91.
Gleicher N, Weghofer A, Barad DH. Dehydroepiandrosterone (DHEA) reduces embryo aneuploidy: direct evidence from preimplantation genetic screening (PGS). Reprod Biol Endocrinol. 2010;8:140.

*Primary Examiner* — Amy Bowman
(74) *Attorney, Agent, or Firm* — Davidoff Hutcher & Citron LLP; David H. Siegel

(57) ABSTRACT

Method of selecting oocyte donor candidates for oocyte donation. A number of triple CGG repeats on each allele of the isolated FMR1 gene is measured by using an assay, and an oocyte donor is selected for oocyte donation only if both alleles of the isolated FMR1 gene have more than 26 CGG repeats.

12 Claims, 13 Drawing Sheets

|  | Donors | Infertility Patients | P |
|---|---|---|---|
| Number | 233 | 354 | |
| Age (years) | 24.4 ± 3.3 | 33.5 ± 3.5 | <.0001 |
| AMH (ng/ml) | 4.3 ± 2.6 | 1.9 ± 2.1 | <.0001 |
| FSH (mIU/ml) | N/A | 13.2 ± 17.3 | |
| BMI | 21.4 ± 2.4 | 24.4 ± 5.5 | <.0001 |
| FMR1 n (%)<br>*norm*<br>*het-norm/ low*<br>*het-norm/ high*<br>*hom-low/ low*<br>*hom-high/ high*<br>*hom-low/ high* | 127 (54.5)<br>50 (21.5)<br>29 (12.5)<br>8 (3.4)<br>10 (4.3)<br>9 (3.9) | 209 (59.0)<br>66 (18.6)<br>62 (17.5)<br>10 (2.8)<br>2 (0.6)<br>5 (1.4) | 0.005 |

| Parameter | | Estimate | Standard Error | t value | Pr > \|t\| |
|---|---|---|---|---|---|
| Intercept | | 1.7669 | 0.3012 | 5.87 | <.0001 |
| *FMR1* | *het-norm/high* | 0.0716 | 0.1275 | 0.56 | 0.5747 |
| *FMR1* | *het-norm/low* | -0.0030 | 0.1011 | -0.03 | 0.9766 |
| *FMR1* | *hom-high/high* | -0.2526 | 0.1984 | -1.27 | 0.2043 |
| *FMR1* | *hom-low/high* | -0.1699 | 0.2100 | -0.81 | 0.4192 |
| *FMR1* | *hom-low/low* | -0.7202 | 0.2202 | -3.27 | 0.0012 |
| *FMR1* | *norm* | 0.0000 | . | . | . |
| Age | | -0.0190 | 0.0124 | -1.53 | 0.1277 |

FIG. 5

| Parameter | | Estimate | Standard Error | Z | Pr > \|Z\| |
|---|---|---|---|---|---|
| Intercept | | 2.1464 | 0.2797 | 7.67 | <.0001 |
| *FMR1* | *het-norm/high* | 0.1240 | 0.1134 | 1.09 | 0.2744 |
| *FMR1* | *het-norm/low* | -0.0053 | 0.0990 | -0.05 | 0.9575 |
| *FMR1* | *hom-high/high* | -0.4046 | 0.1146 | -3.53 | 0.0004 |
| *FMR1* | *hom-low/high* | -0.2722 | 0.3407 | -0.80 | 0.4244 |
| *FMR1* | *hom-low/low* | -0.8938 | 0.3258 | -2.74 | 0.0061 |
| Age | | -0.0349 | 0.0113 | -3.08 | 0.0020 |

FIG. 6

| Effect | FMR1 | Estimate | Standard Error | t value | Pr > \|t\| |
|---|---|---|---|---|---|
| Intercept | | 2.2358 | 0.4514 | 4.95 | <.0001 |
| Time | | -0.0908 | 0.0294 | -3.09 | 0.0030 |
| *FMR1* | *low* | -0.0912 | 0.0896 | -1.02 | 0.3129 |
| *FMR1* | *norm and high* | 0 | . | . | . |
| Time* *FMR1* | *low* | -0.1338 | 0.0657 | -2.04 | 0.0463 |
| Time* *FMR1* | *norm or high* | 0 | . | . | . |
| Age(baseline) | | -0.0119 | 0.0123 | -0.96 | 0.3403 |
| BMI | | -0.0307 | 0.0170 | -1.80 | 0.0768 |

FIG. 7

| Δ | $\bar{X} \pm SD$ |
|---|---|
| Δ norm | 1.39(±1.28) |
| Δ het-norm/low | 1.75(±1.31) |
| Δ het-norm/high | 1.29(±1.13) |
| Δ hom-low/low | 0.87(±0.74) |
| Δ hom-high/high | 1.13(±1.32) |
| Δ hom-low/high | 2.17(±0.87) |

SCREENING OF OOCYTE DONOR CANDIDATES BASED ON THE FMR1 GENE

CROSS REFERENCE TO RELATED APPLICATIONS

This application is a continuation-in-part of U.S. patent application Ser. No. 14/101,646, filed on Dec. 10, 2013, which is a divisional of U.S. patent application Ser. No. 13/612,566, filed on Sep. 12, 2012, now U.S. Pat. No. 8,629,120, which is a continuation-in-part of U.S. patent application Ser. No. 13/360,349, filed on Jan. 27, 2012, which is a continuation-in-part of U.S. patent application Ser. No. 13/043,199, filed on Mar. 8, 2011, and of U.S. patent application Ser. No. 12/508,295, filed on Jul. 23, 2009, all of which are incorporated by reference herein.

BACKGROUND

1. Field of the Invention

The present invention relates generally to methods for selecting oocyte donors by evaluating CGG repeats on the fragile X mental retardation 1 (FMR1) gene. Particularly, the present invention provides methods for selecting oocyte donor candidates for oocyte donation and/or excluding oocyte donor candidates from oocyte donation based on a candidates' FMR1 genotype.

2. Description of the Related Art

The following acronyms are used throughout this specification:
AIRE: Autoimmune Regulator
CGG: Cytosine-Guanine-Guanine
DHEA: Dehydroepiandrosterone
FMR1: Fragile X Mental Retardation 1
FMRP: Fragile X Mental Retardation Protein
FOR: Functional Ovarian Reserve
FXS: Fragile X Syndrome
GnRH: Gonadotropin Releasing Hormone
GnRH-a: Gonadotropin Releasing Hormone Agonist
OPOI: Occult Primary Ovarian Insufficiency
OR: Odds Ratio
POA: Premature Ovarian Aging
POF: Premature Ovarian Failure
POI: Primary Ovarian Insufficiency
POS: Premature Ovarian Senescence
TOR: Total Ovarian Reserve These acronyms also appear after the first use of each full term.

The FMR1 gene (gene location Xq27.3) is commonly studied or analyzed because of its association with Fragile X Syndrome (FXS). FXS is the most common cause of familial mental retardation and autism (see, Bagni C., Tassone F., Neri G., Hagerman R., *Fragile X Syndrome: Causes, Diagnosis, Mechanisms, and Therapeutics*, The Journal of Clinical Investigation, December 2012, 4314-22, hereinafter referred to as "Bagni"). FXS occurs when the FMR1 gene is inactivated and does not produce Fragile X Mental Retardation Protein (FMRP). FMRP is important for proper neurological development and is involved in RNA translation. This inactivation is usually caused by too many Cytosine-Guanine-Guanine (CGG) trinucleotide repeats on the FMR1 gene. FMR1 genes are usually classified by the number of CGG repeats on the gene. The usual classification in current medical practice recognizes four ranges of CGG repeats on the FMR1 gene: a normal (or common) range of $CGG_{n<45}$, an intermediate range of $CGG_{n\sim45\text{-}54}$, a premutation range of $CGG_{n\sim55\text{-}200}$ and a full mutation range of $CGG_{n>200}$. FXS usually occurs in persons with an FMR1 gene in the full mutation range. A gene in the premutation range can expand to the full mutation range in the next generation of offspring (see, Willemsen R., Levenga J., Oostra B. A., *CGG Repeat in the FMR1 Gene: Size Matters*, Clinical Genetics, September 2011; 214-25, hereinafter referred to as "Willemsen"). Because of such expansion, FXS risk screening focuses on women with FMR1 genes in the premutation range, who are at risk for having children with FXS. FXS risk screening is the primary purpose of FMR1 testing in current medical practice.

Y. H. Fu found a peak in the population distribution of CGG repeats in the range $CGG_{n=29\text{-}30}$ (see, Fu Y. H., Kuhl D. P., Pizzuti A., et al., *Variation of the CGG Repeat at the Fragile X Site Results in Genetic Instability: Resolution of the Sherman Paradox*, Cell, December 1991; 1047-58, hereinafter referred to as "Fu"). The inventors herein investigated a connection between the FMR1 gene and ovarian function based on the distribution peak at $CGG_{n=29\text{-}30}$. Ovarian effects of the FMR1 gene are supported by a known association between FMR1 genotypes in the premutation range ($CGG_{n\sim55\text{-}200}$) and Primary Ovarian Insufficiency (POI), also known as Premature Ovarian Failure (POF) (see, Gleicher N., Weghofer A., Barad D. H., Defining Ovarian Reserve to Better Understand Ovarian Aging. Reproductive Biology and Endocrinology, February 2011, 23, hereinafter referred to as "Gleicher I"). A recent study of a mouse FMR1 homologue also supports the association of the FMR1 gene with ovarian aging (see, Hoffman G. E., Le W. W., Entezam A., et al. *Ovarian Abnormalities in a Mouse Model of Fragile X Primary Ovarian Insufficiency*. The Journal of Histochemistry and Cytochemistry, June 2012, 439-56).

The inventors defined new ranges of CGG repeats on the FMR1 gene relevant to ovarian health: a normal (norm) range of $CGG_{n=26\text{-}34}$, a low range of $CGG_{n<26}$ and a high range of $CGG_{n>34}$. Further refinement of these ranges defined norm (both alleles in normal range), heterozygous (het, one allele in and the other outside normal range) and homozygous (hom, both alleles outside normal range) genotypes. Het and hom genotypes were further subdivided into high or low. For example, a female with a het-high genotype has one FMR1 allele with more than 34 CGG repeats and one FMR1 allele with 26-34 CGG repeats. Cross-sectional studies demonstrate associations between the various genotypes described above and specific ovarian aging patterns (see, Gleicher N., Weghofer A., Barad D. H., *Ovarian reserve Determinations Suggest New Function of FMR1 (Fragile X Gene) in Regulating Ovarian Ageing*. Reproductive Biomedicine Online, June 2010, 768-75, hereinafter referred to as "Gleicher II"; Gleicher N., Weghofer A., Lee I. H., Barad D. H., *FMR1 Genotype With Autoimmunity-Associated Polycystic Ovary-Like Phenotype and Decreased Pregnancy Chance*. PloS One, December 2010, e15303, hereinafter referred to as "Gleicher III"; Gleicher N., Weghofer A., Lee I. H., Barad D. H., *Association of FMR1 Genotypes With in Vitro Fertilization (IVF) Outcomes Based on Ethnicity/Race*, PloS One, April 2011, e18781, hereinafter referred to as "Gleicher IV"; and Gleicher N., Weghofer A., Kim A., Barad D. H., *The Impact in Older Women of Ovarian FMR1 Genotypes and Sub-Genotypes on Ovarian Reserve*, PloS One, March 2012, e33638, hereinafter referred to as "Gleicher V"). These associations are more fully disclosed herein. Genotype/phenotype interactions are usually studied in homozygous subjects, but these studies have so far only studied norm and het women because all three hom sub-genotypes, combined (high/high, high/low and low/low), occur in less than 10 percent of women, not enough to provide a significant population size for study (see, Gleicher II, Gleicher III, Gleicher IV and Gleicher V). These new range and genotype definitions allow the use of the FMR1 gene to assess ovarian health.

Human females are typically tested to determine ovarian health and to assess their fertility only if they are experiencing infertility, at risk for infertility based on age and/or are indicated to have ovarian aging by showing signs of ovarian aging. These tests are for Anti-Müllerian Hormone (AMH) and/or Follicle Stimulating Hormone (FSH) levels. The tests are performed once and the human female's level of AMH and/or FSH is compared against the normal range for human females of her age. If AMH is lower than the normal range or FSH is higher than normal the normal range, the human female is considered to have Premature Ovarian Aging (POA), also known as Occult Premature Ovarian Insufficiency (OPOI). These AMH/FSH tests, however, are generally not performed in young human females, defined herein to mean human females who have not experienced infertility and are not otherwise indicated to have ovarian aging.

Because testing for ovarian health is presently performed only when the human female already experienced infertility and/or is indicated for ovarian aging by showing symptoms of infertility, such as menstrual irregularities, the diagnosis of POA or POF is usually only obtained when the POA is at advanced clinical stages, after POF has occurred or when the human female is about 38 years or older. As a result, there is an absence of prospective risk assessments in adolescent and young adult females even though approximately 10% of human females will suffer from premature ovarian aging. At advanced clinical stage or advanced age, even advanced fertility treatments for POA demonstrate limited success, and egg donation remains the only realistic choice for women with POF (see, Gleicher I). Late diagnosis, of course, assumes further significance in older, often single, women because POA further compounds the negative effects of advanced age. As a result, late diagnosis of POA leads to limited success in treatment.

Earlier diagnosis of premature ovarian aging presents many benefits for women, most notably, earlier and potentially more effective treatment options (see, Cil A. P., Bang H., Oktay K., *Age-Specific Probability of Live Birth With Oocyte Preservation: An Individual Patient Data Meta-Analysis*, Fertility and Sterility, August 2013, 492-9). Identification of human females likely to be affected by POA when their ovarian reserve is still relatively normal offers a choice between childbirth at a younger age than they otherwise planned or fertility preservation by assisted reproductive technologies. All methods of fertility preservation are more efficient at younger than at older ages and, therefore, less costly and more cost-effective. The reduced cost is especially important given ever-increasing medical costs and the present high cost of infertility testing and treatment, which, in many cases, is not covered by health insurance.

Fertility preservation for young women is relatively recent and resulted from a need by women who became infertile after undergoing cancer treatment but who still desired to have children. Fertility preservation emerged to provide young cancer survivors a reproductive future (see, Waimev K. E., Duncan F. E., Su H. I., Smith K., Wallach H., Jona K., Coutifaris C., Gracia C. R., Shea L. D., Brannigan R. E., Chang R. J., Zelinski M. B., Stouffer R. L., Taylor R. I., Woodruff T. K., *Future Directions in Oncofertility and Fertility Preservation: A Report From the* 2011 *Oncofertility Consortium Conference*, Journal of Adolescent and Young Adult Oncology, March 2013, 25-30). Aside from fertility preservation for cancer patients, women are delaying childbirth for various social and personal reasons and use fertility preservation to have children later in life (see, Donnez J., *Introduction: Fertility Preservation, from Cancer to Benign Disease to Social Reasons: The Challenge of the Present Decade*, Fertility and Sterility, May 2013, 1467-1468; and Cobo A., Garcia-Velasco J. A., Domingo J., Remohl J., Pellicer A., *Is Vitrification of Oocytes Useful for Fertility Preservation for Age-Related Fertility Decline and in Cancer Patients?* Fertility and Sterility, May 2013, 1485-1495). Fertility preservation in response to causes of infertility other than cancer or voluntary delay, such as endometriosis, is also entering medical practice (see, Bedoschi G., Turan V., Oktay K., *Fertility Preservation Options in Women with Endometriosis*, Minerva Ginecologica, April 2013, 99-103). However, fertility preservation in response to other causes of infertility, such as premature ovarian aging, has not yet received attention because premature ovarian aging was not predictable by the existing knowledge in the art.

Ovarian aging is the combination of declines in oocyte quality and oocyte number. Ovulation, the maturation and release of oocytes, begins at menarche, the onset of menstrual cyclicity. Menarche is the start of a complex process of steady follicle recruitment that organizes recruited follicles into maturing monthly cohorts, groups of follicles in the same stage of development. In natural ovulation cycles, follicular cohorts mature over 2-4 months, resulting in ovulation of a single dominant follicle in each cohort. Other follicles in each cohort undergo degeneration and apoptosis (see, FIG. 1), resulting in unifollicular ovulation. The ovary's ability to organize cohesive monthly cohorts of follicles of similar sizes and maturity is a characteristic of young age and normal ovarian function. The ability to organize and carry out monthly unifollicular ovulation diminishes with advancing female age and/or in association with POA (and possibly early stages of POF). Older females and patients with POA have more inhomogeneous follicle sizes and oocyte maturity distribution than females who are young and not experiencing POA. This difference is shown in IVF studies for those two populations (see, Gleicher I).

As FIG. 1 shows, the current medical understanding holds that females are born with a limited pool of follicles, also known as the total ovarian reserve (TOR), that depletes throughout life until menopause. TOR peaks in intrauterine life at approximately 7 million follicles/oocytes with significant depletion before birth. Females have less than 1 million follicles/oocytes at birth and by menarche approximately only 400,000 remain in the female. The speed of ovarian depletion slows between menarche and menopause, when only a few hundred to one thousand follicles/oocytes remain in the ovaries (see, Gleicher I).

A patient's TOR is primarily the large pool of unrecruited, primordial follicles "resting" at a very primitive stage. A patient's recruited follicles (also called "growing" follicles) are a much smaller part of TOR known as the Functional Ovarian Reserve (FOR). After weeks to months of maturation, the recruited follicles reach maturity in either natural or ovarian stimulation cycles. A patient's TOR and FOR deplete over time and reflect the patient's ovarian age.

The speed of follicle recruitment is statistically correlated to the number of remaining primordial follicles. Therefore, the size of the pool of growing follicles (representing FOR) also correlates with speed of recruitment (see, Gleicher V; Gleicher I; and Nelson S. M., Anderson R. A., Broekmans F. J., Raine-Fenning N., Fleming R., La Marca A., *Anti-Müllerian Hormone: Clairvoyance or Crystal Clear?* Human Reproduction, March 2012, 631-636, hereinafter referred to as "Nelson I"). AMH is produced in the granulosa cells of these small growing follicles and inhibits follicle recruitment and growth (see, Gleicher I; Ledger W. L., *Clinical Utility of*

*Measurement of Anti-Müllerian Hormone in Reproductive Endocrinology*. Journal of Clinical Endocrinology & Metabolism, December 2010, 5144-5154, hereinafter referred to as "Ledger"; and Gleicher N., Weghofer A., Barad D. H., *The Role of Androgens in Follicle Maturation and Ovulation Induction: Friend or Foe of Infertility Treatment?* Reproductive Biology and Endocrinology, August 2011, 116). Because of this connection between AMH and the small growing follicles, a human female's AMH levels reflect the size of her pool of small growing follicles. Age-specific AMH levels, which reflect age-specific follicle pool size, are known in the art (see, Barad D. H., Weghofer A., Gleicher N., *Utility of Age-Specific Serum Anti-Müllerian Hormone Concentrations*, Reproductive Biomedicine Online, March 2011, 284-291, hereinafter referred to as "Barad"; and Kelsey T. W., Wright P., Nelson S. M., Anderson R. A., Wallace W. H. B., *A Validated Model of Serum Anti-Müllerian Hormone from Conception to Menopause*, PLoS One 2011, e22024, hereinafter referred to as "Kelsey").

Additionally, the gene that controls the AMH type II receptor (AMHR2) is also associated with follicle recruitment, further connecting AMH to follicle recruitment (see, Voorhuis M., Broekmans F. J., Fauser B. C., Onland-Moret N. C., van der Schouw Y. T., *Genes Involved in Initial Follicle Recruitment May be Associated With Age at Menopause*, Journal of Clinical Endocrinology & Metabolism, March 2011, 473-479). Because of the connection of AMH to follicular recruitment and growth, AMH levels are widely considered to best reflect TOR (see, Ledger; Nelson I). Because TOR is the primary component of ovarian age, low AMH levels are indicative of ovarian aging and AMH levels below normal for a particular age are indicative of POA.

Because of the association of AMH with FOR and TOR, an AMH test with levels below age-specific normal levels can indicate POA. As discussed above, POA affects approximately 10% of all women, and can have different causes, including, but not limited to, the factors set forth in Table 1:

TABLE 1

KNOWN CAUSES OF PREMATURE OVARIAN AGING

Low number of follicles/oocytes at birth/menarche
Known genetic causes
Excessive follicle recruitment
Anti-ovarian autoimmunity
    Autoimmune oophoritis
    Anti-ovarian autoimmunity
    Autoimmune polyglandular syndromes
    Turner syndrome
Space occupying lesions
    Endometriosis
    Ovarian tumors
Iatrogenic interventions
    Surgery
    Chemotherapy
    Radiation therapy
    Bone marrow transplantation
    Anti-viral therapies As Table 1 shows, aside from iatrogenic (caused by medical treatment) follicle/oocyte losses and ovarian tissue loss from space-occupying lesions, POA has other causes, such as excessively rapid recruitment of follicles, low follicle numbers at birth and/or menarche, genetic disorders and anti-ovarian autoimmunity. Both low follicle numbers at birth and excessively rapid recruitment are under strong genetic control. The other major causes of POA, as discussed below, are also under genetic control.

Approximately one-third of POA cases are caused by anti-ovarian autoimmunity (see, Gleicher N., Weghofer A., Oktay K., Barad D., *Do Etiologies of Premature Ovarian Aging (POA) Mimic Those of Premature Ovarian Failure (POF)?* Human Reproduction, October 2009, 2395-2400). Anti-ovarian autoimmunity is well-known in humans with Addison's disease who develop autoimmune (lymphocytic) oophoritis, autoimmune polyglandular syndromes (APS), and Turner's syndrome. (see, Hoek A., Schoemaker J., Drexhage H. A., *Premature Ovarian Failure and Ovarian Autoimmunity*, Endocrinology Review, February 1997, 107-134, referred to hereinafter as "Hoek"). Hoek also reveals that ovaries are often subject to an autoimmune attack that is statistically associated with thyroid autoimmunity, anti-adrenal autoimmunity and other, often non-organ-specific, autoimmune responses. The X chromosome's role as an autoimmune chromosome also explains the association of autoimmunity and Turner syndrome (see, Bianchi I., Lleo A., Gershwin M. E., Invernizzi P., *The X Chromosome and Immune Associated Genes*, Journal of Autoimmunity, May 2012, 187-192; Bukalov V. K., Gutin L., Cheng C. M., Zhou J., Sheth P., Shah K., Arepalli S., Vanderhoof V., Nelson L. M., Bondy C. A., *Autoimmune Disorders in Women with Turner Syndrome and Women with Karyotypically Normal Primary Ovarian Insufficiency*, Journal of Autoimmunity, June 2012, 315-322; and Lleo A., Moroni L., Caliari L., Invernizzi P., *Autoimmunity and Turner's Syndrome*, Autoimmune Review, May 2012, 538-543). Therefore, autoimmune attacks on the ovaries are known in the art, but their precise mechanisms are not well understood.

Autoimmune-associated POA is most understood in combination with autoimmune polyendocrine syndrome type 1 (APS-1), also known as polyendocrinopathy candidiasis ectodermal dystrophy or Whitaker syndrome. It is caused by a mutation in the Autoimmune Regulator (AIRE) gene (see, Michels). This gene is of crucial importance in the thymus, where it regulates the process that prevents T cells from attacking a human's own cells. AIRE mutations that interfere with normal AIRE activity are associated with attacks against a human's own cells. The connection between AIRE and POA is supported by animal models. AIRE gene knockout mice experience early follicle depletion by age 20 weeks and complete follicle depletion (POF/POI) in 50-60% of animals. Therefore, AIRE appears crucial for preventing POA, and mutations in the gene de-inhibit follicle maturation, leading to the rapid depletion discussed above. Because of AIRE's strong association with autoimmunity, impaired fertility in the AIRE knockout mouse model can be attributed to immune-mediated loss of TOR. Such immune-mediated loss of TOR is caused by autoimmune attacks on the ovaries, thereby destroying the oocyte reserve. The AIRE gene is the first gene associated with autoimmune-induced POA (see, Michels; and Cushman R. A., *Evidence That the Autoimmune Regulator Gene Influences Thymic Production of Ovarian Antigens and Prevents Autoimmune-Mediated Premature Reproductive Senescence*, Biology of Reproduction, April 2012, 109).

Genes involved in follicle recruitment, such as AIRE, appear to limit over-recruitment of primordial follicles, which can rapidly deplete unrecruited follicles. When genes that affect follicle recruitment in either rodents or humans are mutated, blocked or knocked out, primordial follicles are over-recruited and deplete rapidly. Genes involved in follicle recruitment also influence a female's age at menopause. These genes appear to reduce the rate of follicular recruitment. Slower recruitment preserves more follicles/oocytes, leading to better remaining TOR at later ages.

Because of the link between autoimmunity and ovarian aging, any autoimmunity in females must be considered a risk factor for POA. Moreover, because autoimmunity is highly familial, a patient's family history of autoimmunity is also a risk factor. This includes a familial history of repeated pregnancy loss, often the consequence of abnormal immune system activation.

In addition to familial autoimmunity, other genetic influences on ovarian aging are well-demonstrated. Age at menopause is correlated between mothers and daughters and between pairs of sisters (see, van Asselt K. M., Kok H. S., Pearson P. L., Dubas J. S., Peeters P. H., Te Velde E. R., van Noord P. A., *Heritability of Menopausal Age in Mothers and Daughters*, Fertility and Sterility, November 2004, 1348-1351; and Morris D. H., Jones M. E., Schoemaker M. J., Ashworth A., Swerdlow A. J., *Familial Concordance for Age at Natural Menopause; Results From the Breakthrough Generations Study*, Menopause, September 2011, 956-961). Additionally, age at menarche, which is also genetically influenced, relates to risk for POA (see, Weghofer A., Kim A., Barad D. H., Gleicher N., *Age at Menarche: A Predictor of Diminished Ovarian Function*, Fertility and Sterility, October 2013, 1039-1043). Therefore, whether a human female's mother or sister(s) entered menopause early and/or a human female's own young age at menarche are also risk factors for POA.

IVF is the creation of an embryo outside a human female's body from an oocyte harvested from a human female. The created embryo is then implanted in a human female, referred to as the IVF patient. The oocyte may be harvested from the IVF patient, in which case it is called an autologous oocyte, or it may be harvested from another human female, in which case the IVF patient is the recipient and the human female the oocyte was harvested from is the donor. Oocyte donors are selected from a pool of oocyte donor candidates who apply to donate oocytes. Donor selection is based on interviews and medical testing of candidates. Genetic testing to exclude genetic defects in embryos produced by IVF, including FMR1 testing to exclude FXS, is performed in oocyte donors after they are selected.

Related Studies

A longitudinal study studied the association of low ($CGG_{n<26}$) alleles of the FMR1 gene, carried by approximately one-quarter of all females, with POA and female infertility. This study is summarized in the article entitled FMR1 *Gene Mutations Already at Young Ages Are Predictive Of Later Premature Ovarian Senescence and Infertility* (Kushnir V. A., Yao Y., Himaya E., Barad D. H., Weghofer A., Lee H. J., Wu Y. G., Shohat-Tal A., Lazzaroni-Tealdi E., Gleicher N., FMR1 *Gene Mutations Already at Young Ages Are Predictive Of Later Premature Ovarian Senescence and Infertility*, 2013, hereinafter referred to as the "longitudinal study" and included as Appendix A). Females carrying such alleles can now be identified at young ages as at risk for imminent POA and infertility. Such women can then undergo specific treatment and/or testing regimens, based on their FOR, until a diagnosis of POA is either confirmed by additional hormonal testing or until testing indicates that there is no clinical basis for a diagnosis of POA. Women whose deviation from normal levels of FOR is confirmed can be counseled at young ages when fertility preservation is more efficient, effective and less costly as compared with older women. This provides such women options of advancing pregnancies or of pursuing fertility preservation by oocyte and/or ovary freezing at younger ages than currently performed. Accordingly, fertility outcomes are improved.

By analyzing the FMR1 genes of young human females, young human females can be identified as at risk of POA and/or infertility and a hormone testing regimen based on the young human females' FMR1 genotypes can be performed. If the testing indicates that the young human female has POA, the young human female can then be treated. The treatment for POA may be any treatment or treatments for a human female who has experienced infertility or is at risk for infertility based on age, even though the human female does not currently exhibit such infertility. Examples of such treatment are disclosed in Gleicher II, Gleicher III, Gleicher IV and Gleicher V and other references mentioned herein and include, without restriction, oocyte cryopreservation, hormonal treatment, and/or gene therapy.

Approximately 10 percent of all females are affected by POA (see, Gleicher I). Many of those affected will seek infertility treatment. Early diagnosis of impending POA would allow such women to either change their reproductive life schedule and/or take fertility-preserving steps, like oocyte cryopreservation (see, Donnez J., *Introduction: Fertility Preservation, From Cancer to Benign Disease to Social Reasons: the Challenge of the Present Decade*, Fertility and Sterility, May 2013, 1467-8). Both of these options are more patient-friendly, effective and economical than the current practice of treating POA after POA progresses to an advanced stage.

The data in the longitudinal study allowed for analysis of how the FMR1 genotype is indicative of imminent ovarian aging in human females who have not experienced infertility and are not otherwise indicated to have POA. The data was correlated to progression of ovarian aging over a significant span of a human female's life and enabled highly accurate prediction of the expected onset of ovarian aging. Such accurate prediction allows treatment when ovarian aging is in its early stages or even before it begins to affect a human female's reproductive ability.

In addition to the prediction of imminent ovarian aging, the longitudinal data obtained during the study allows for prediction of female infertility. A female is considered infertile after trying and failing to become pregnant for at least a year. Many women who experience infertility have POA. As such, early predictions based on the longitudinal data of the study enabled the development of treatment and/or testing regimens of human females for infertility before they are infertile.

More particularly, the longitudinal study investigated functional ovarian reserve (FOR), as reflected by AMH levels, relative to FMR1 genotypes/sub-genotypes in 233 consecutive oocyte donor candidates, who underwent 233 baseline and 122 repeat AMH measurements (355 total measurements), and 354 consecutive infertility patients under 38 (mean age 35.5±3.5 years), who underwent 354 baseline AMH measurements. The 354 infertile women served as a cross-sectional comparison group to assess effects of FMR1 mutations on later occurring female infertility. Sixty-six donors had multiple longitudinal assessments over approximately 4 years, typically at substantially uniform intervals (e.g., yearly). Donor candidates with presumed increased reproductive risks based on medical, family and genetic histories were excluded.

FMR1 genotypes and sub-genotypes are defined in Gleicher II, Gleicher III, Gleicher IV and Gleicher V. By defining a normal $CGG_{n=26-34}$ range, all $CGG_n$ below and above that range are considered abnormal. A female with both FMR1 alleles in normal range, therefore, is norm, a female with one within and one outside normal range is het and a female with both alleles outside norm range is hom. Whether an allele is above (high) or below (low) normal range further sub-divides het and hom genotypes (het-norm/high, het-norm/low, hom-high/high, hom-high/low, hom-low/low) into sub-genotypes. Table 2 provides the definitions of the terms for FMR1 alleles and genotypes used herein.

TABLE 2

CGG Repeat Counts and FMR1 Genotypes

| | One Allele | Other Allele | Genotype/Sub-genotype |
|---|---|---|---|
| (CGG 26 ≤ n ≤ 34 = norm) | High | High | Hom-high/high |
| | High | Norm | Het-norm/high |
| (CGG n > 34 = high) | High | Low | Hom-high/low |
| | Norm | Norm | Norm |
| (CGG n < 26 = low) | Norm | Low | Het-norm/low |
| | Low | Low | Hom-low/low |

The longitudinal study had two purposes. The first purpose was to assess potential impacts of FMR1 genotypes/sub-genotypes on POA, also called Occult Primary Ovarian Insufficiency (OPOI) (see, Gleicher I). To avoid contamination by the effects of physiologic ovarian aging, only infertile women under age 38 years were included in the study. The second purpose was to determine whether differences in distribution of FMR1 genotypes/sub-genotypes between younger oocyte donors and older infertility patients are influenced by the increasing risk of experiencing infertility with advancing age. The 354 consecutive infertility patients below age 38 years (mean age 33.5±3.5 years) served as an older cross-sectional comparative group to assess whether the speed of decline in FOR, as measured by the size of the decreases in AMH (Δ AMH), differed between FMR1 genotypes and sub-genotypes and whether the prevalence of individual FMR1 genotypes and sub-genotypes differed between donor and infertility patient populations.

The longitudinal study found that donors with both alleles with a low CGG count ($CGG_{n<26}$) (hom-low/low) demonstrated significantly lower AMH levels than donors with normal CGG counts (both alleles $CGG_{n=26-34}$, norm). The het-low FMR1 genotype was associated with more rapid declines in AMH levels than the norm genotype or het-high FMR1 genotype. The Δ AMH significantly differed between the young donor subjects and the older infertility subjects and among het-norm/low, norm and het-norm/high populations. The overall distribution of the FMR1 genotypes and sub-genotypes also differed between young donor subjects and older infertility subjects.

The longitudinal study assessed effects on FOR of all FMR1 genotypes and sub-genotypes. In the longitudinal study, the difference in Δ AMH between young human female donors and older infertility patients was determined for the FMR1 genotypes/sub-genotypes. The longitudinal study showed that the hom FMR1 genotypes and het-low sub-genotypes identify young females at risk for POA. POA is a major cause of female infertility that affects approximately 10% of all women, and is only diagnosed at advanced stages, when potential interventions are less effective and more costly than they would be at earlier stages.

FIG. 3 summarizes characteristics of the egg donor subjects (human females who have not experienced infertility and are not otherwise indicated to have POA, as defined above) and known infertility patients. The mean age of women at the time of the baseline measurements was 24.4±3.3 years for the egg donors and 33.5±3.5 years for the infertility patients. The age of human females within the donor and infertility patient groups did not vary significantly for different FMR1 genotypes and sub-genotypes. Mean AMH at the baseline measurement was 4.3±2.6 for the donor human females and 1.9±2.1 ng/mL for the infertile patients. Mean body mass indices (BMI) at the baseline measurement were 21.4±2.4 for the donor human females and 24.4±5.5 kg/m² for the infertile patients.

Baseline AMH values are the values in the initial AMH testing for each subject, performed after her FMR1 gene was isolated and the number of CGG repeats on both alleles of the FMR1 gene were determined. The FMR1 and AMH tests were performed by routine commercial assays, as described in Gleicher II, Gleicher III, Gleicher IV and Gleicher V. The age of each donor/infertile patient was recorded with her first AMH collection. AMH values were logarithmically transformed to provide a normal distribution and to obtain a new variable, $\log_{AMH}$. FIG. 3 shows a histogram for AMH for all 355 donor samples. Repeat AMH tests were performed if a donor was matched with an IVF candidate more than six months after the initial AMH test. Values from these repeat tests were statistically adjusted, including adjustments for age. This provided baseline values for all subjects of the longitudinal study and repeat AMH values for many subjects.

In FIG. 3, the p-value for Age, AMH and BMI is based on two independent sample t-tests of the distribution of means of donors and infertility patients. The p-value for FMR1 n % is based on a chi-square test related to the distribution of FMR1 sub-genotypes of donors vs. infertility patients. The p-values of the correlations show that the FMR1 sub-genotypes and AMH are strongly correlated.

Donors and infertile patients differed significantly in age, AMH and BMI values (all P<0.001; see, FIG. 3). Low mean AMH and high mean FSH values in the infertile patient group reflect an infertility patient population with very poor fertility characteristics based on those hormone levels. Full ($CGG_{n>200}$) and premutation range alleles ($CGG_{n\sim55-200}$) were almost absent in both subject groups with 1 case in each group. The high alleles ($CGG_{n>34}$) in the FMR1 data, therefore, primarily represent CGG values in the ranges $CGG_{n<45}$ or $CGG_{n\sim45-54}$, and the correlations are not due to FXS, which appears in persons with full mutation range FMR1 genotypes.

The relationship between AMH and FMR1 genotypes/sub-genotypes was examined while accounting for the age variations among the subjects. Repeated AMH measurements, age and FMR1 genotype/sub-genotype were collected from the 233 donor candidates. A generalized estimating equation (GEE) model, using the norm FMR1 genotype as a reference level, was used to study the effect of FMR1 genotypes/sub-genotypes on AMH while accounting for correlations within subjects. A linear mixed-effect (LME) model was used to confirm the results provided by GEE. The results of the GEE and LME models are reported in FIGS. 5-7.

Short-term (approximately 4 years) time-related AMH changes were investigated using a LME model based on repeated AMH measurements in donors. Long-term (approximately 10 years) time-related AMH changes were studied by comparing baseline AMH values between donor candidates and infertility patients. The AMH baseline decline Δ AMH was calculated. Baseline AMH in donors with the norm genotype was higher than in donors with the hom-low/low sub-genotype (P=0.001), but did not differ from other FMR1 sub-genotypes (See, FIG. 3). A statistical comparison of repeated measurements of donor AMH between norm and all other FMR1 sub-genotype using a GEE model revealed a difference between norm and hom-high/high (p<0.001) and hom-low/low (p=0.006) (see, FIG. 5). This conclusion was further confirmed by an LME model.

The correlation between FMR1 genotype/sub-genotype and change in AMH level over time is statistically significant (P=0.046) (see, FIG. 7). Based on this correlation, a human female's future decline in AMH levels can be predicted based on her FMR1 genotype. FIG. 8 shows predicted AMH over a 4 year observation period and shows that AMH declines more rapidly in donors with at least one low ($CGG_{n<26}$) allele than in donors with only norm and high alleles. Specifically, FIG. 8 presents the greater predicted decline of AMH over time for women with low vs. norm and high FMR1 genotypes (P=0.046).

This decline in AMH in young human females with at least one low allele indicates that additional testing and treatment for POA and risk of infertility is more useful and productive in such young human females than in other young human females. Early commencement of infertility treatment improves the likelihood of successful conception and pregnancy and is not otherwise performed without early detection of POA.

Young hom-high/high and hom-low/low donors start with lower AMH levels than young norm FMR1 donors. AMH levels decline in all FMR1 genotypes/sub-genotypes between younger oocyte donors and older infertility patients. The decline varies among FMR1 genotypes/sub-genotypes, demonstrating that ovarian aging speed varies based on FMR1 genotypes/sub-genotypes. The statistical comparison of donor AMH baseline between normal alleles and the other FMR1 sub-genotypes, using ANCOVA, showed *P=0.001. The mean and standard deviation of ΔAMH for each FMR1 genotypes/sub-genotypes are summarized in FIG. 9. The ΔAMH for each FMR1 genotype allows prediction of the change over time of a human female's AMH levels based on her FMR1 genotype.

Because of the small total number of subjects with hom FMR1 genotypes, hom-high/high, hom-high/low and hom-low/low were combined. ANCOVA was used to compare the distribution between genotypes and remaining het sub-genotypes. The results show a statistically significant difference in the decline in ΔAMH between human females with the het-norm/low sub-genotype and the norm genotype (P=0.045) or the het-norm/high genotype (P=0.042) (see, FIG. 10). The data is presented as a mean and a standard error of mean. The absence of a statistically significant difference between het-norm/low and hom FMR1 sub-genotypes is likely due to the small number of hom sub-genotypes. This is further supported by individual AMH values in the hom-high/low donor group, where AMH levels were either high or low, resulting in a mean value for all hom-high/low subjects in between these two extremes even though individual human females with the hom-high/low FMR1 genotype did not exhibit such in-between levels. The resulting mean is probably not representative of gene activity.

FIG. 11 shows the ΔAMH and the statistical significance of all pairwise comparisons of ΔAMH between the FMR1 genotypes. Decline in FOR, as measured by ΔAMH, is associated with FMR1 low genotypes/sub-genotypes in younger oocyte donors and older infertility patients. More rapid declines in FOR lead to more female infertility and, therefore, either to more or less observed infertility treatments. Fewer infertility treatments will be observed if patients with a particular FMR1 genotype dropped out of treatment before inclusion in this study (see, Gleicher N., Weghofer A., Kim A., Barad D. H., *Comparison of Ovarian FMR1 Genotypes and Sub-Genotypes in Oocyte Donors and Infertile Women*, Journal of Assisted Reproduction and Genetics, June 2012, 529-32). The relative absence of infertility patients with the FMR1 low genotypes associated with poor ovarian reserve and poor IVF outcomes in the infertility patients indicates their early drop-out from infertility treatments. This is because such patients are unlikely to achieve successful pregnancy, and are likely to receive discouraging results early in infertility treatment. This would be especially prevalent in a highly adversely selected patient population, such as the population of the longitudinal study (see, FIG. 2). That is, a young human female with a low number of CGG repeats on one or both alleles of the FMR1 gene would be expected to benefit from treatment for infertility, but would be expected to abandon such treatments when they were unsuccessful, and a young human female with a normal number of CGG repeats on both alleles of the FMR1 gene would not be expected to seek treatment for infertility.

The data from the longitudinal study supports the increased drop-out rate of infertility patients with particular FMR1 genotypes. The largest drop-out rates were seen in hom-high/high (4.3% to 0.6%), hom-low/low (3.4% to 2.8%), hom-high/low (3.9% to 1.4%) and het-norm/low (21.5% to 18.6%) FMR1 genotypes/sub-genotypes, which are also associated with abnormally low FOR in young oocyte donors. By contrast, women with norm FMR1 genotypes (54.5% to 59.0%) and het-norm/high (12.5% to 17.5%) sub-genotypes increased in prevalence among infertility patients. The het-norm/high is associated with comparatively good preservation of FOR into older ages (see, Gleicher V). These changes in the overall distribution of FMR1 genotypes and sub-genotypes were statistically significant (P=0.005), suggesting that women with unfavorable FOR at young ages drop out of infertility treatments earlier than women with normal FOR for their age. This further demonstrates the importance of providing treatment for infertility and/or POA at young ages and before infertility is experienced.

A low ($CGG_{n<26}$) allele, as in a het-norm/low patient, appears to reduce pregnancy chances by approximately half in comparison to patients with the norm genotype (see, Gleicher III). Young women, however, have high FOR that masks the reduced FOR in young women with FMR1-low genotypes. Therefore, infertility does not become clinically apparent until older age, and even detection of the reduced FOR is difficult in young women (Gleicher N., Weghofer A., Barad D. H., *Intermediate and Normal Sized CGG Repeat on the FMR1 Gene Does not Negatively Affect Donor Ovarian Response*, Human Reproduction, July 2012, 2241-2; author reply 2-3, hereinafter referred to as "Gleicher VI"; Gleicher N., Kim A., Barad D. H., et al. *FMR1-Dependent Variability of Ovarian Aging Patterns is Already Apparent in Young Oocyte Donors*, Reproductive Biology and Endocrinology, August 2013, 80, hereinafter referred to as "Gleicher VII"; and Lledo B., Guerrero J., Ortiz J. A., et al. *Intermediate and Normal Sized CGG Repeat on the FMR1 Gene Does not Negatively Affect Donor Ovarian Response*. Human Reproduction, February 2012, 609-14, hereinafter referred to as "Lledo").

The results of the longitudinal study confirm the importance of the FMR1 gene in female reproductive aging. The most important conclusion is that analyzing the FMR1 gene at a young age allows a determination of risk of POA and infertility, and the targeted treatment of young human females. The longitudinal study demonstrates that, in young human females, significant differences in AMH levels are apparent only in association with the hom-low ($CGG_{n<26}$) FMR1 genotype. Over 4 years of longitudinal follow-up, donors with the hom-high ($CGG_{n<26}$) FMR1 genotype demonstrated significantly reduced FOR in comparison to norm donors. Single het-low donors demonstrated significantly greater ΔAMH compared to norm donors (see, FIG. 10).

FIGS. 5 and 9 show the data of longitudinal versions of earlier cross-sectional studies (see, Gleicher VI; Gleicher VII;

and Lledo). FIGS. 5 and 9 show that young human females who are oocyte donors with norm and het FMR1 genotypes demonstrate similar FOR. Only young human females with the hom-low/low sub-genotype have significantly lower baseline FOR than young human females with the norm FMR1 genotype (FIG. 11). Only a few years later, all hom sub-genotypes (except hom-high/low) and women with even a single low ($CGG_{n<26}$) allele are adversely affected in comparison to either norm or high ($CGG_{n>34}$) allele-carrying women (see, FIGS. 11 and 12).

These findings also confirm that women with het-norm/low sub-genotypes rapidly recruit follicles at young ages, leading to quick depletion of FOR and early ovarian aging (see, Gleicher III). AMH is considered the best tool to assess FOR (see, Nelson II). Actively recruiting het-low women demonstrate relatively high AMH values at young ages (FIG. 11). The two low alleles in hom-low/low females produce a more severely affected ovarian phenotype characterized by significantly depleted FOR. Women with the hom-low/low genotype have FOR loss as severe at young ages as the FOR loss seen at middle-age in women with het-low genotypes, as described in the cross sectional studies discussed in Gleicher III. Accordingly, women with the hom-low FMR1 genotype are more likely than women with het-low genotypes to experience infertility.

FIGS. 10 and 11 confirm previously noted longitudinal observations of rapid declines in AMH in het-norm/low women. Het-norm/low women experience a much larger ΔAMH than norm and het-norm/high women. Hom-low/low women's AMH levels decline less than those of het-norm/low females, but start from a very low baseline at young ages. Het-norm/low females actively recruit oocytes at very young ages and continue to do so into middle-age (see, Gleicher III).

The longitudinal study also indicates a difference in the ΔAMH between het-norm/low and het-norm/high, demonstrating a profound divergence in ovarian aging phenotypes after young donor ages. While het-low sub-genotypes continue to rapidly deplete FOR, het-high sub-genotypes slow their depletion. As a result, women with het-norm/high sub-genotypes have unexpectedly good FOR at very advanced ages (see, Gleicher V).

As previously noted, the statistical similarity in ΔAMH between het-norm/low and hom women is attributable to small patient numbers. Moreover, patients with the hom-high/low sub-genotype further distort the data because they are evenly split between high and low FOR. FOR is determined in patients with the hom-high/low sub-genotype by which allele undergoes X chromosome-inactivation and, likely, how methylated the active X chromosome is. This sub-genotype, therefore, requires careful additional longitudinal AMH evaluations before the risk for POA can be determined.

The longitudinal study further found that analysis of FMR1 genotypes/sub-genotypes in young human females allows the detection of risk of POA and appropriate treatment. Women found to be at risk for POA based on their FMR1 genotype can be carefully followed with AMH and/or other tests of ORe, including FSH and/or androgens, recently associated with low ovarian reserve. This allows for earlier diagnosis and treatment if the tests indicate that such treatment is necessary (see, Gleicher N., Kim A., Weghofer A., et al., *Hypoandrogenism in Association with Diminished Functional Ovarian Reserve*, Human Reproduction, April 2013, 1084-91).

Finally, the longitudinal study indicated that, in a very adversely selected patient population, such as the infertile women of the longitudinal study, women with disproportionally quick ovarian aging FMR1 genotypes/sub-genotypes drop out of infertility treatment early. This further demonstrates the importance of early diagnosis of POA to allow for timely interventions by either enhanced conception planning and/or fertility preservation by oocyte freezing or other evolving technologies.

The longitudinal study supports the proposition that slower follicle recruitment preserves more follicles/oocytes, leading to better remaining TOR at later ages. As demonstrated by the study, low FMR1 gene alleles are associated with early depletion of ovarian reserve and resulting POA/OPOI. That is, in the study, for the young oocyte donors, homozygous (hom) donors with two low alleles demonstrated significantly reduced FOR by their early 20's. Young heterozygous (het) donors with only one low allele demonstrated significantly accelerated loss of FOR in comparison with donors who only had high and/or norm alleles. By contrast, high alleles appear to preserve FOR into advanced female ages (see, Gleicher V). Analysis of FMR1 genotype in young human females is predictive of imminent ovarian aging patterns.

In high-risk patients, the availability of age-specific normal AMH values allows for longitudinal monitoring of TOR. If patients deviate from normal AMH levels at their ages, such longitudinal monitoring allows the diagnosis of POA at significantly younger ages than was previously possible. It is currently unknown what percentage of females between the ages of 16-21 would be found to be at increased risk of POA by such a screening process, and how many amongst those would develop POA. Considering an approximate 10% prevalence of POA in the general population, the number of patients at risk is expected to be large.

All of the publications mentioned above, as well as those mentioned below, are incorporated by reference herein.

SUMMARY OF THE INVENTION

A method for selecting oocyte donors comprises performing an FMR1 gene test on oocyte donor candidates and selecting oocyte donor candidates as oocyte donors or rejecting them as oocyte donors based on the analysis of their FMR1 gene. The method is based on the results of a study (the "IVF study") described in the article entitled *Utilizing FMR1 Gene Mutations As Predictors Of Treatment Success In Human In Vitro Fertilization*, which is incorporated by reference in its entirety. (See, *Utilizing FMR1 Gene Mutations As Predictors Of Treatment Success In Human In Vitro Fertilization*, V. A. Kushnir, Y. Yu, D. H. Barad, A. Weghofer, E. Himaya, H-J Lee, Y-G Wu, A. Shohat-Tal, E. Lazzaroni-Tealdi, N. Gleicher, 2014, and appended hereto as Appendix B).

As used herein, an oocyte donor candidate is a human female who has volunteered to donate eggs, oocytes and/or embryos but has not been previously selected as an egg, oocyte and/or embryo donor and has not been added to the egg, oocyte and/or embryo donor pool. As used herein, an oocyte donor is a human female who is in the egg, oocyte and/or embryo donor pool, whether or not they have ever donated any eggs, oocytes, embryos and/or any other biological material.

As discussed in the detailed description of the invention, a human female's FMR1 genotype indicates the likely morphological quality of an embryo created from an oocyte harvested from that human female and/or the likelihood that clinical pregnancy will result from the implantation of an embryo created from an oocyte harvested from that human female. When the FMR1 test indicates that the embryos created from oocytes harvested from the oocyte donor candidate are likely to be of poor morphological quality or less likely than other embryos to result in clinical pregnancy when implanted, the oocyte donor candidate is rejected as an oocyte donor.

Importantly, the FMR1 test is performed before the oocyte donor candidate is selected as an oocyte donor. For example, the FMR1 test is performed before the oocyte donor candidate is matched with an oocyte or embryo recipient and before the oocyte donor candidate receives any ovarian stimulation or other preparation for induced ovulation or oocyte harvesting.

BRIEF DESCRIPTION OF THE DRAWINGS

FIG. 5 is a table of parameter estimates showing the associations between the FMR1 genotypes and ovarian aging, calculated by analysis of covariance (ANCOVA) of AMH baselines of the donors in the longitudinal study;

FIG. 6 is a table of parameter estimates showing the associations between the FMR1 genotypes and ovarian aging, calculated by a GEE of AMH assessments in the donors in the longitudinal study;

FIG. 7 is a table of estimates showing the associations between the FMR1 genotypes and ovarian aging, calculated by an LME model of AMH assessments in the donors in the longitudinal study;

DETAILED DESCRIPTION OF THE INVENTION

Figure 1:
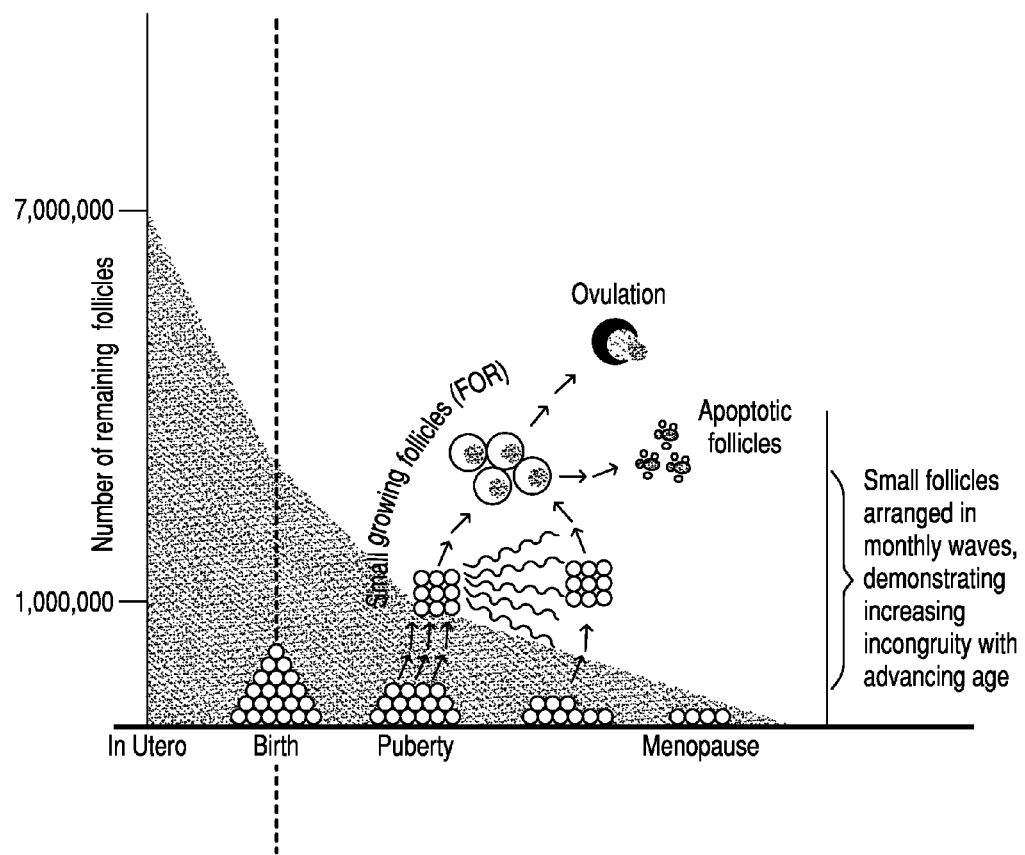
FIG. 1 is a graph depicting the ovulation process and showing a relationship between follicle/oocyte numbers in human females and age.
Figure 2:
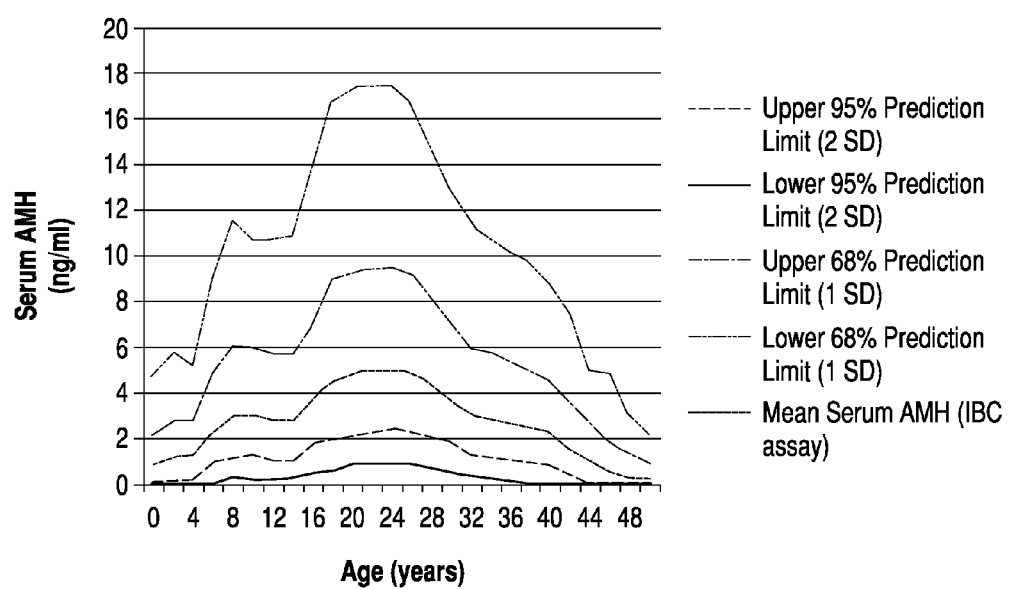
FIG. 2 is a graph of mean AMH levels over time and age of human females with confidence intervals.
Figures 3, 4:
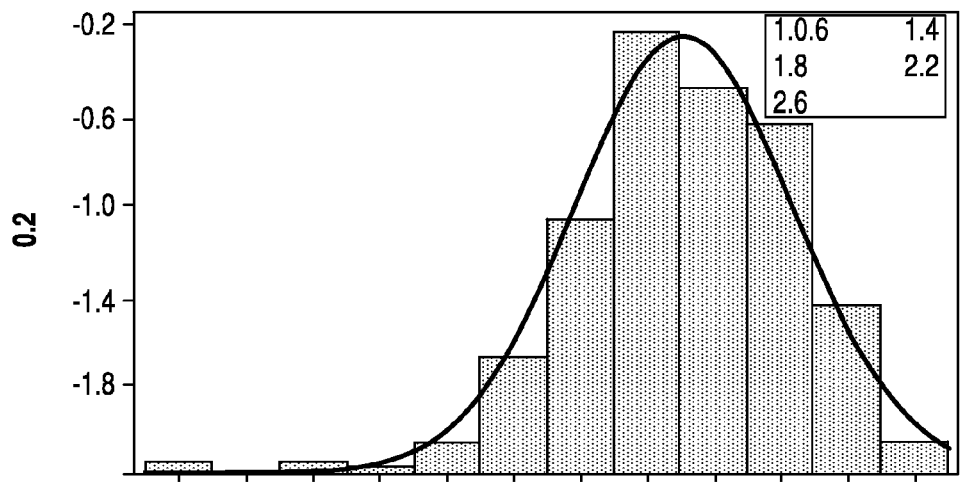
FIG. 3 is a table showing baseline characteristics and FMR1 genotypes of oocyte donor candidates and infertility patients and distribution of FMR1 genotypes/sub-genotypes in the longitudinal study.
FIG. 4 is a histogram of log(AMH) values in the donors in the longitudinal study.
Figure 8:
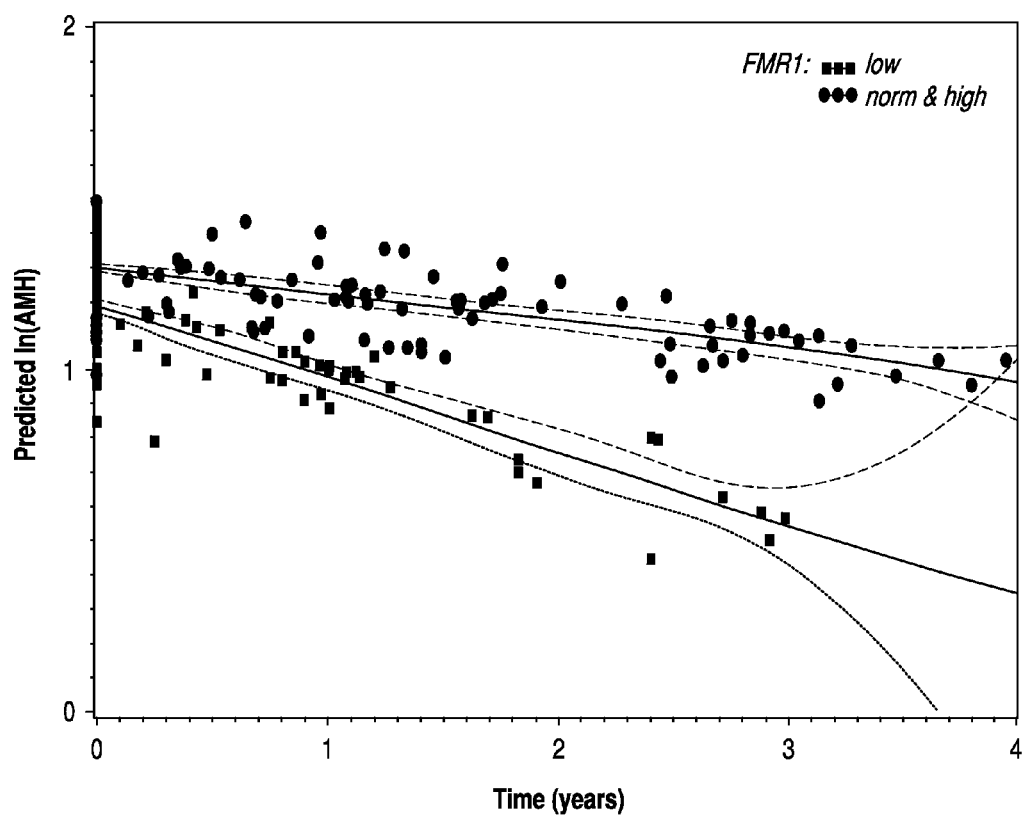
FIG. 8 is a graph showing the different patterns of AMH change over time in donors with and without an FMR1 low allele as demonstrated by repeat longitudinal AMH measurement in the donors in the longitudinal study separated by FMR1 genotypes/sub-genotype.
Figures 9, 10:
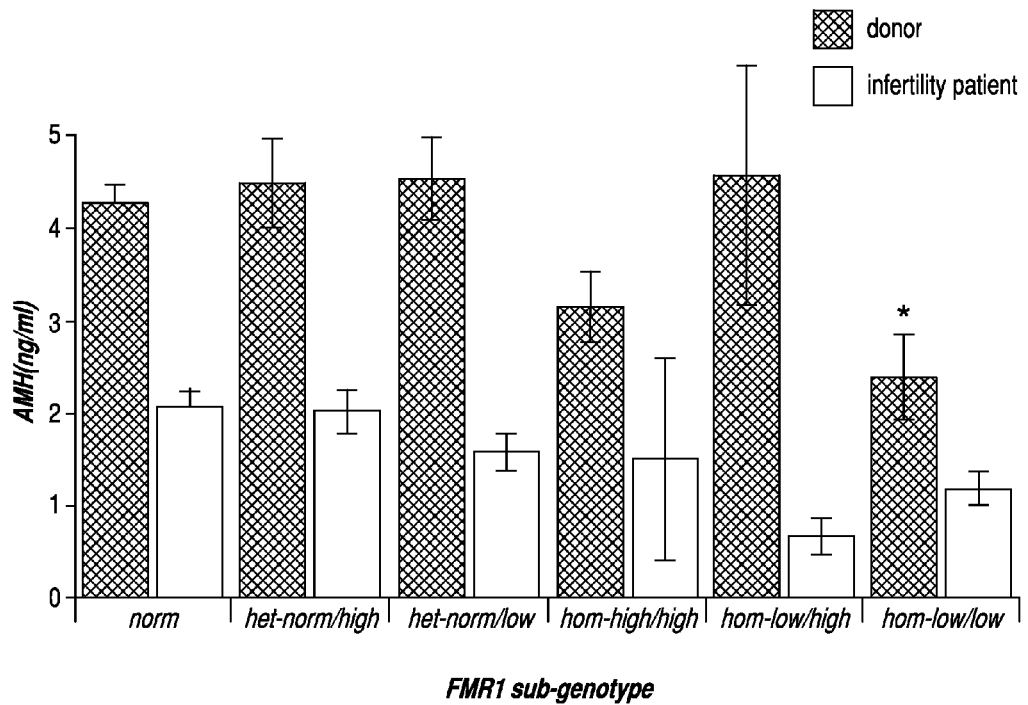
FIG. 9 is a histogram of the prevalence of the FMR1 sub-genotypes in oocyte donors and infertility patients in the longitudinal study.
FIG. 10 is a table showing the mean change in AMH for the subjects with each FMR1 genotype/sub-genotype in the longitudinal study.
Figure 11:
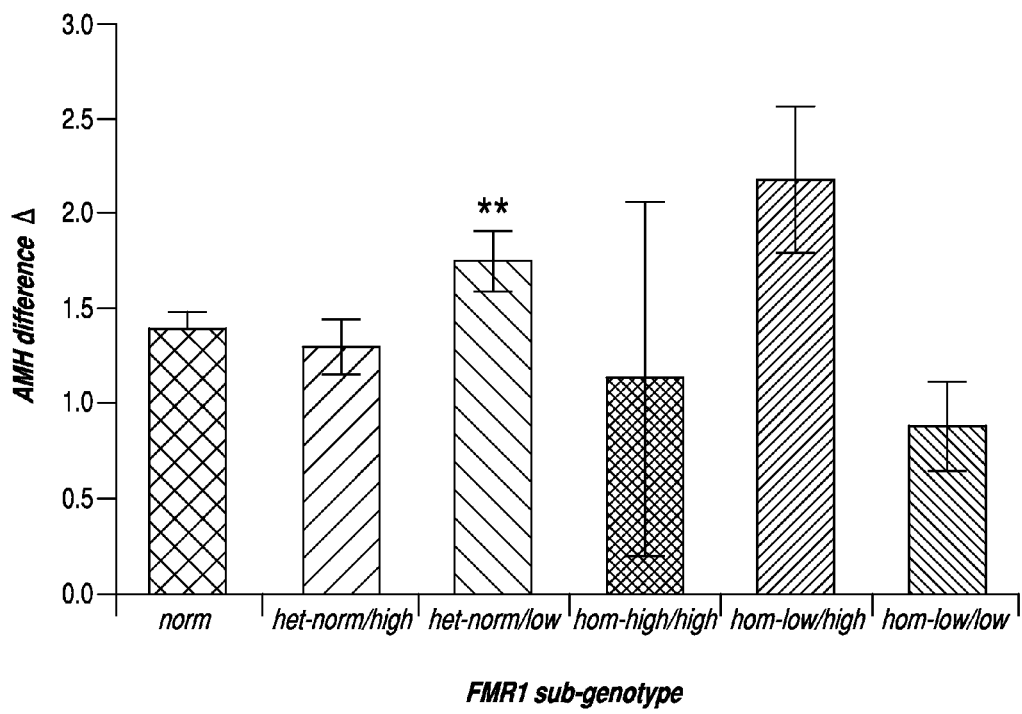
FIG. 11 is a histogram showing the difference in baseline AMH between oocyte donors and infertility patients for each FMR1 genotype.

The present invention comprises a method of selecting oocyte donors and embryo donors. The present invention also comprises a method of screening oocyte donor candidates and embryo donor candidates. The methods are based on the results of the IVF study explained with reference to FIGS. 12-15. The IVF study examined data taken from human female oocyte donors, fertile human females undergoing IVF treatment with autologous oocytes and infertile human females undergoing IVF treatment with donor oocytes. Based on the data of the IVF study, novel techniques for screening oocyte donor candidates and selecting oocyte donors from oocyte donor candidates are described.

The longitudinal study confirmed that young women with low FMR1 alleles are likely to experience POA and infertility. Additionally, young women with low FMR1 alleles who are not diagnosed with POA and/or infertility may be more likely to have impaired fertility compared to other women of their age. Even slightly impaired fertility should be avoided in situations where maximum fertility is required, such as in the selection of women to act as oocyte donors for IVF.

The IVF study has three sub-studies. The first sub-study studied the association between FMR1 genotype and morphologic embryo quality in a sample of 777 embryos in 168 IVF cycles in 125 infertile women of all ages. The second sub-study studied the association between FMR1 genotype and embryo aneuploidy in a sample of 1041 embryos in 149 IVF cycles in presumed fertile women. The third sub-study studied the association between FMR1 genotype and clinical pregnancy rates in 352 infertile patients under age 38 using autologous oocytes in 1st IVF cycles and 179 IVF cycles in patients using donor eggs. All sub-studies accounted for variations in age and all IVF cycles involved standard IVF protocols. Assessments of the number of CGG repeats on the FMR1 gene (CGGn) were performed using commercial assays known in the art. As is standard practice in the art, FMR1 genotypes were not considered when selecting egg donor candidates for donation and/or in selecting treatments for infertile patients. The FMR1 genotypes of the subjects of the IVF study were classified as in Table 2 above. Full mutation (CGGn>200) and premutation range alleles (CGGn=55-200) were absent in investigated populations. The subjects with FMR1 high genotypes have CGG n<55.

Patients and donors underwent standardized ovarian stimulation protocols. Patients under age 40 with normal FOR received full doses (1.0 mg/0.1 mL) of gonadotropin releasing hormone agonist (GnRH-a; Lupron®, Abbot Pharmaceuticals, North Chicago, Ill.) and ovarian stimulation with up to 300 IU of gonadotropins daily, usually half as FSH and half as human menopausal gonadotropins (hMG). Patients with diminished FOR and/or low serum androgens and those over age 40 received at least six weeks of dehydroepiandrosterone (DHEA) supplementation with 25 mg of pharmaceutical grade, micronized DHEA three times a day prior to the start of their IVF cycle. The IVF cycles in patients with diminished FOR and/or low serum androgens and those over age 40 included prevention of premature ovulation with microdose GnRH-a (50 µg/0.1 mL, twice a day) and ovarian stimulation with 300-450 IU FSH and 150 IU of hMG daily. Oocyte donors received full doses of GnRH-a (1.0 mg/0.1 mL) and ovarian stimulation with up to 300 IU of hMG daily. Final oocyte maturation was triggered in all cycles with 5,000-10,000 IU of human chorionic gonadotropin (hCG).

After oocytes were harvested and embryos were created from the harvested oocytes, embryos were examined for morphology at the cleavage stage once the embryo started dividing but not growing. Cleavage stage embryos were classified as having good morphology (4 cells d-2, 8 cells d-3, little or no fragments), poor morphology (arrested embryos or >25% fragmented) or fair morphology (all other embryos). The aneuploidy or euploidy of embryos was determined by Pre-implantation Genetic Screening (PGS). PGS was performed in a group of 121 fertile women undergoing a total of 149 IVF cycles for non-infertility related reasons, primarily to choose the gender of a child (elective gender selection). Embryos were biopsied for quality on day three after fertilization at 6-8 cell stages. Fluorescence in situ hybridization (FISH) was utilized with probes for the X, Y, 13, 16, 18, 21 and 22 chromosomes.

Because presence of low alleles ($CGG_{n<26}$) in prior studies impacted FOR and pregnancy chances in fertility treatment, analyses in the IVF study primarily compared patients with low alleles to those without low alleles, (i.e., those with only norm and high FMR1 alleles). Generalized linear mixed effect (GLME) models were used to examine the statistical associations between embryo morphology and FMR1 genotype and between embryo ploidy and FMR1 genotype. GEE models were utilized to confirm GLME statistical results. A logistic regression model was used to study the clinical pregnancy rate of first IVF treatments in infertility patients under age 38. All the foregoing statistical analyses were adjusted for female age. The analysis of embryo morphology was also adjusted for number of prior treatment cycles. Covariates were considered statistically significant when P values were <0.05 using SAS 9.2.

FMR1 and Morphological Embryo Quality 777 embryos from 125 women in 168 IVF cycles in infertile women of all ages were examined for morphological qualities. Table 3, below, summarizes the characteristics of the subjects. This infertile patient group was not restricted in age and the mean age of group members was 39.7±5.7 years. 45.4% of all embryos were considered good quality, 43.4% fair quality and 11.2% poor quality. Women with low sub-genotypes were overrepresented and those with high sub-genotype and norm genotypes underrepresented in comparison to other studies.

TABLE 3

Subject Characteristics in Embryo Morphology Group

| Variables | $\overline{X}$ ± SD or n (%) | | |
|---|---|---|---|
| Number of patients | 125 | | |
| Number of cycles | 168 | | |
| Age (years) | 39.7 ± 5.7 | | |
| Number of embryos | 777 | | |
| Embryo quality (Good/Fair/Poor) | 353 (45.4%)/337 (43.4%)/87 (11.2%) | | |

| FMR1 Genotype as Defined in Table 2: | Patients n (%) | Cycles n (%) | Embryos n % |
|---|---|---|---|
| norm | 51 (40.8%) | 60 (35.7%) | 319 (41.1%) |
| het-norm/high | 25 (20.0%) | 34 (20.2%) | 144 (18.5%) |
| hom-high/high | 1 (0.8%) | 1 (0.6%) | 3 (0.4%) |
| het-norm/low | 37 (29.6%) | 56 (33.3%) | 234 (30.1%) |
| hom-low/low | 4 (3.2%) | 6 (3.6%) | 41 (5.3%) |
| hom-low/high | 7 (5.6%) | 11 (6.6%) | 36 (4.6%) |

Figure 12:
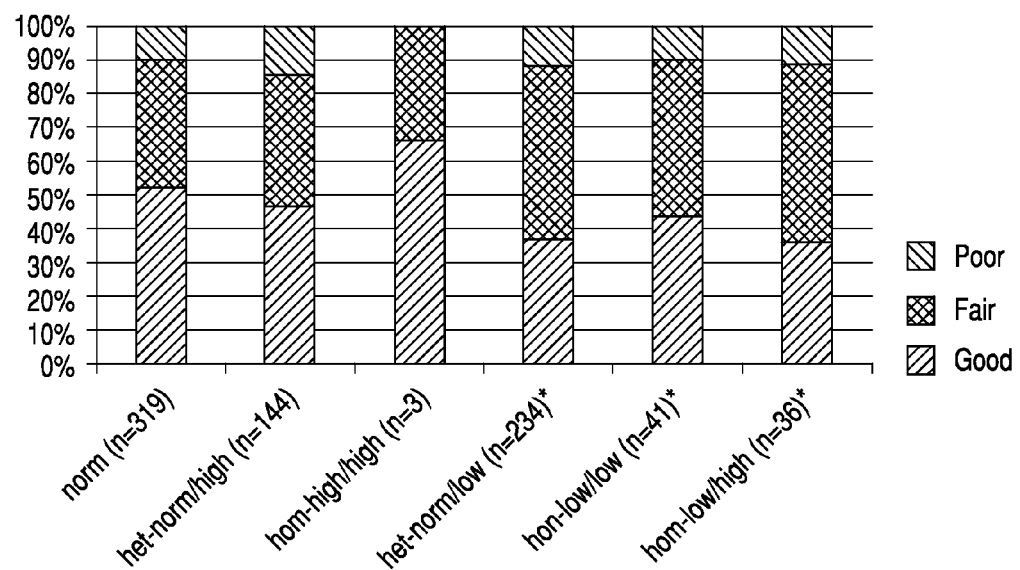
FIG. 12 is a histogram showing the distribution of morphologic embryo quality among subjects in the IVF study with the various FMR1 genotypes and sub-genotypes.

FIG. 12 summarizes morphologic embryo quality, based on FMR1 genotypes/sub-genotypes. Comparing availability of good quality embryos to availability of fair and poor quality embryos, embryos in patients with at least one low FMR1 allele were statistically likely to be of lower morphologic quality than embryos in patients with only norm and high alleles (P=0.03). The odds ratio (OR) estimate of having good morphologic quality embryos vs. having fair and/or poor quality embryos between low and norm and/or high genotypes/sub-genotypes was 1.637. This odds ratio indicates that patients with only norm and/or high alleles had a 63.7% higher probability of producing good morphologic quality embryos than patients with at least one low FMR1 allele.

FMR1 and Embryo Aneuploidy Rates

Embryo ploidy represents a substantial component of total functional embryo quality. Embryo ploidy was assessed in 1,041 embryos from 149 IVF cycles in presumably fertile women. These women were presumed fertile because they were undergoing IVF with pre-implantation genetic diagnosis (PGD) for non-infertility related reasons, mostly elective gender determination. The women were presumed to be fertile because they were undergoing IVF for reasons other than infertility. This patient group were of mid-range ages (33.5±5.5 years), which is younger than the infertility patients in the embryo morphology group. Table 4 summarizes the characteristics of these subjects in the ploidy group.

TABLE 4

Subject Characteristics in Embryo Ploidy Group

| Variables | $\overline{X}$ ± SD or n (%) | | |
|---|---|---|---|
| Patients | 121 | | |
| Number of cycles | 149 | | |
| Age (years) | 33.5 ± 5.5 | | |
| Number of embryos | 1041 | | |
| Ploidy (normal/abnormal) | 571 (54.9%)/470 (45.2%) | | |

| FMR1 sub-genotypes as defined in Table 2: | Oocyte source n (%) | Cycles n (%) | Embryos n (%) |
|---|---|---|---|
| norm | 71 (58.7%) | 85 (57.1%) | 646 (62.1%) |
| het-norm/high | 19 (15.7%) | 23 (15.4%) | 141 (13.5%) |
| hom-high/high | 2 (1.7%) | 3 (2.0%) | 26 (2.5%) |
| het-norm/low | 26 (21.5%) | 34 (22.9%) | 193 (18.5%) |
| hom-low/low | 2 (1.7%) | 2 (1.3%) | 16 (1.5%) |
| hom-low/high | 1 (0.8%) | 2 (1.3%) | 19 (1.8%) |

As show in Table 4, the FMR1 genotype distribution in these presumably fertile female subjects differed from the infertile patients in the embryo morphology portion of the study (P<0.001). Specifically, the distribution in the ploidy group had predominantly more norm genotypes and fewer het, as well as hom, FMR1 mutations with low and/or high alleles than the infertile patients in the embryo morphology group. The distribution in the ploidy group is closer to previously studied distribution patterns in the general population. The increased rate of low alleles in the infertile patients in the embryo morphology group suggests an association between low alleles and infertility in older women.

Figure 13:
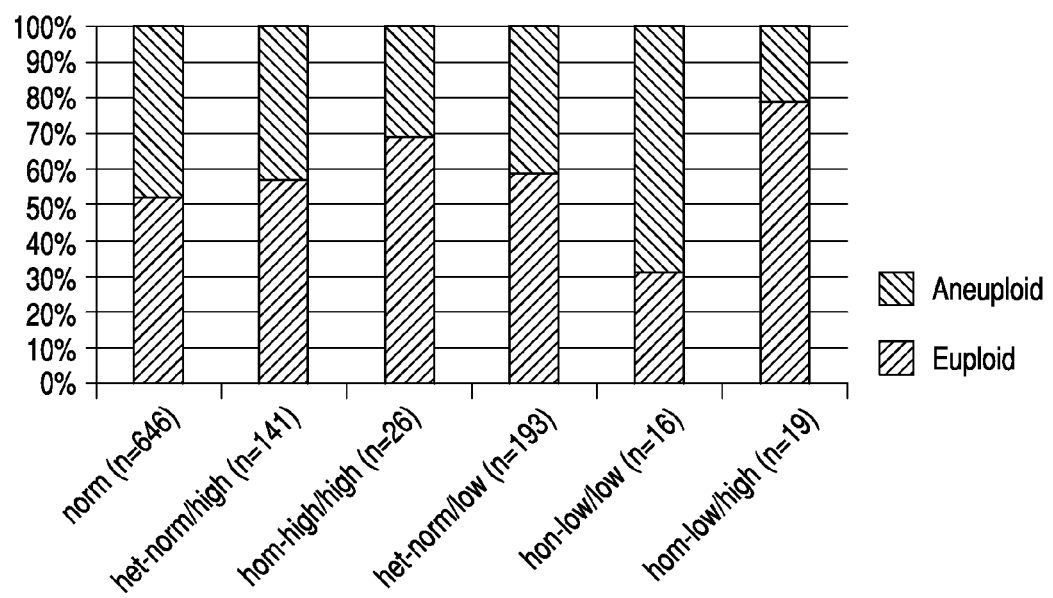
FIG. 13 is a histogram showing the distribution of aneuploidy rates among subjects in the IVF study with each FMR1 genotype.

FIG. 13 shows the distribution of aneuploidy rates among human females in this group with each of the FMR1 genotypes. No statistical differences in aneuploidy rate were noted between women with low and/or norm and high alleles (OR, 0.855; 95% CI 0.578, 1.266; P=0.434). Hom-low women, however, demonstrated unusually high aneuploidy rates compared to women with other FMR1 genotypes, suggesting that the lack of significant findings for hom-low women may be due to relatively small study subject numbers. Also, the very low aneuploidy number in women with one low and one high allele suggests a potential compensatory effect of a high allele on the negative effects of a low allele.

The age of the women yielding oocytes was statistically related to aneuploidy (OR 1.041; 95% CI 1.011, 1.072; P=0.007). A one-year increase in age resulted in a 4.1% higher chance of embryo aneuploidy. The association between female age and increasing aneuploidy rates is known in the art. The lack of an association between embryo ploidy and the female's FMR1 genotype suggests that the relationship demonstrated between morphologic embryo quality and FMR1 mutations is independent and not based on embryo ploidy.

FMR1 and Clinical Pregnancy Rates

FMR1 genotypes/sub-genotypes are predictive of IVF pregnancy chances in infertile women. (See Gleicher, N., Weghofer, A., Lee I H, Barad DH, *Association of FMR1 Genotypes with In Vitro Fertilization (IVF) Outcomes Based on Ethnicity/Race*, PLoS One, April 2011). IVF pregnancy chances are also associated with embryo quality. The data from the embryo morphology group demonstrates that norm and/or high FMR1 alleles are associated with significantly more good quality embryos than low alleles. Accordingly, the FMR1 gene probably affects IVF pregnancy chances by affecting oocyte/embryo quality.

IVF pregnancy chances can also be significantly affected by implantation, an immunologically-influenced process. Low FMR1 alleles in infertile women are also associated with abnormal immune activity in infertile women, suggestive of immune system activation. Because the FMR1 gene may have additional effects on implantation, the IVF study examined how low FMR1 alleles cause lowered IVF pregnancy rates. Specifically, it studied if that association is due to the reduced egg/embryo quality associated with low FMR1 alleles or the implantation effects associated with low FMR1 alleles.

The clinical pregnancy group of the study is middle-aged infertile women under age 38 (mean 33.4±3.4 years) undergoing 352 first autologous IVF cycles (in which the IVF patient receives embryos created from their own oocytes) and 162 infertile IVF patients undergoing 179 donor/recipient IVF cycles (in which the IVF patient receives embryos created from donor embryos). The eggs used were from 162 young oocyte donors (mean donor age 25.0±2.9 years). The clinical pregnancy rate was higher in donor/recipient IVF cycles (55.9%) than in autologous IVF cycles (28.4%; P<0.001).

Distribution of FMR1 genotypes/sub-genotypes significantly differed between the two sub-groups of this clinical pregnancy group (P<0.001). Due to the small sample sizes of hom-low/low, hom-high/high and hom-low/high women, all hom patients in the clinical pregnancy group were combined into one sub-group when comparing the distribution of FMR1 mutations. The younger infertile patient sub-group of the clinical pregnancy group demonstrated a similar distribution of FMR1 genotypes to the presumed fertile women in the ploidy group (see, Table 4). The young oocyte donor sub-group had an FMR1 genotype distribution in-between those two groups and the older infertile patients in the embryo morphological quality group (see, Table 3). The distribution pattern seen in oocyte donors is typical for young normal female populations, suggesting that approximately 22% of young women have low FMR1 alleles and older infertile women have a higher rate of low FMR1 alleles. The increasing prevalence of low alleles in older infertile women, as compared with young donors, points towards an association of low FMR1 alleles with infertility at advanced ages.

Figure 14A:
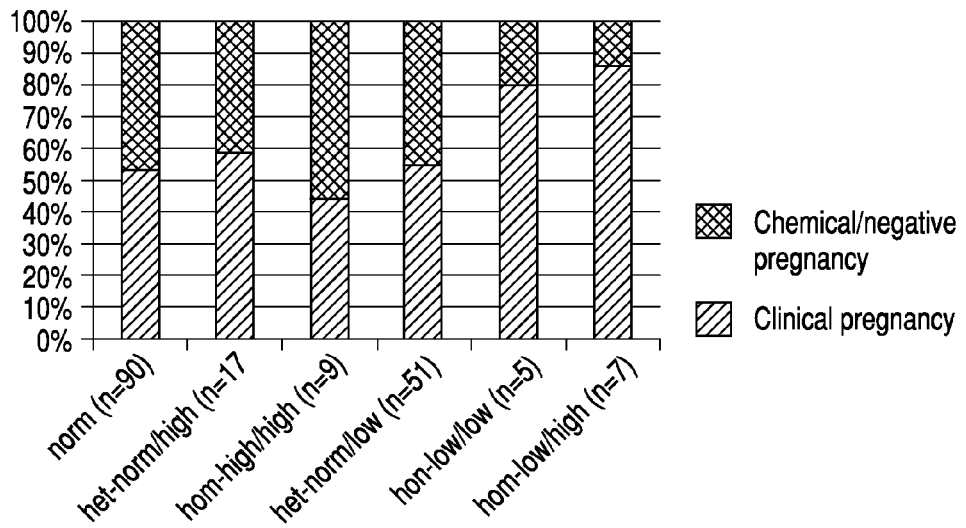
FIG. 14A is a histogram showing clinical pregnancy rates among oocyte donors in the IVF study with each FMR1 genotype.
Figure 14B:
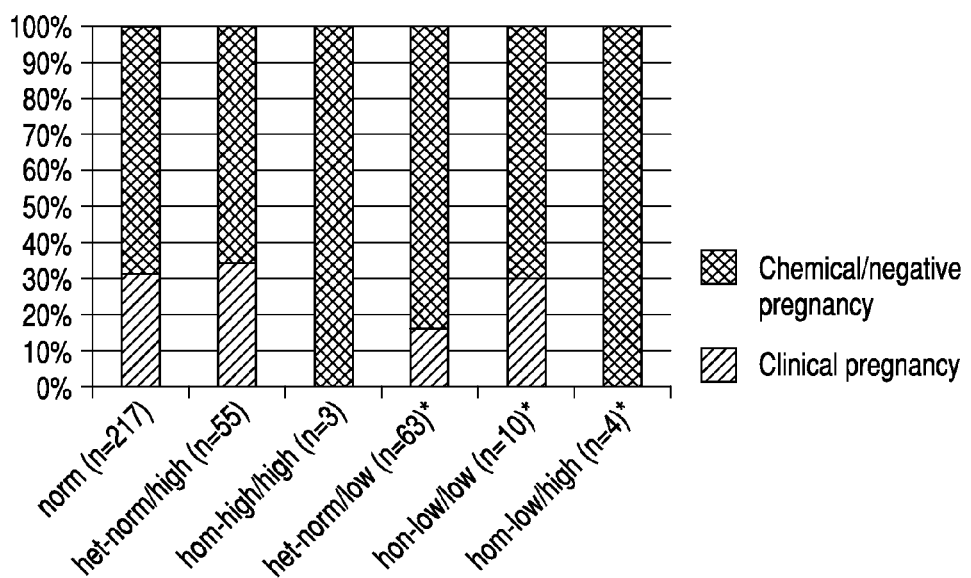
FIG. 14B is a histogram showing clinical pregnancy rates among middle-aged infertile patients in the IVF study with each FMR1 genotype.

FIGS. 14A and 14B show the ratio of clinical pregnancy to biochemical pregnancy (a pregnancy that progresses far enough to cause a positive hormone test but terminates before ultrasound can confirm the pregnancy) or no pregnancy in association with the FMR1 genotypes. Comparing women with at least one low FMR1 allele to those with only norm and high alleles, FIG. 14A shows that, in donor-recipient cycles, the FMR1 mutation of the donor did not directly affect recipient clinical pregnancy rates (OR 0.738; 95% CI 0.387, 1.405; P=0.347). Moreover, FIG. 14A shows that donor ages did not directly affect pregnancy chances (OR 0.970; 95% CI 0.874, 1.078; P=0.568).

Figure 15:
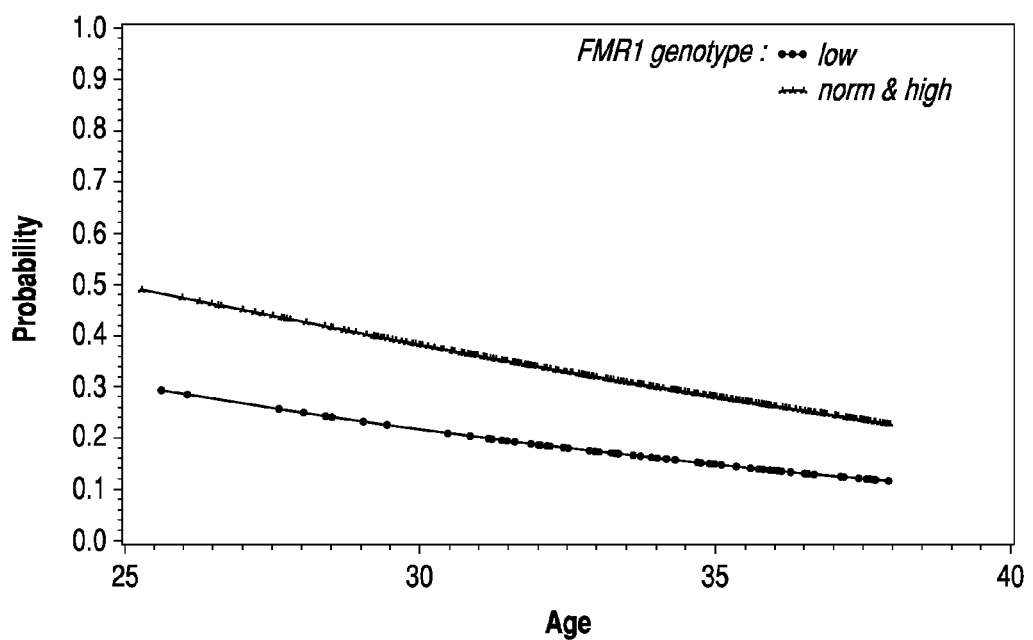
FIG. 15 is a graph showing the predicted probabilities of clinical pregnancy from IVF in infertile patients based on age and FMR1 genotype.

Using a logistic regression model, however, the odds of clinical pregnancy differed significantly in young infertility patients under the age of 38 years between patients with single low FMR1 alleles and those with norm and/or high alleles and no low alleles (OR 2.244; 95% CI 1.168, 4.312; P=0.015; FIG. 14B). The odds ratio of clinical pregnancy vs. biochemical pregnancy or no pregnancy between both groups was 2.244. The odds ratio estimate indicates that women with only norm and/or high FMR1 alleles have 1.244-times higher probability of clinical pregnancy than women with low alleles. FIG. 15 shows that the difference in odds of clinical pregnancy in this relatively young group of infertile women between women with low and with norm/high alleles remains remarkably stable with advancing age, though this difference in odds decreases as women age.

By demonstrating that specific FMR1 gene mutations are associated with morphologic embryo quality and the chance of clinical pregnancy following IVF, the results of the IVF study indicate that the FMR1 gene is the first gene statistically associated with IVF outcomes. This genetic effect of FMR1 on IVF outcomes persists at virtually all ages (see, FIG. 15).

The IVF study demonstrates that the morphologic differences in embryo quality between FMR1 mutations are probably not caused by differences in ploidy. This may explain why embryo morphology is only relatively poorly associated with embryo ploidy and why PGS, which detects aneuploidy, fails to improve IVF outcomes.

The different groups of the IVF study had significant differences in the distribution of FMR1 genotypes. In previous studies of infertile patients, slightly more than half had norm genotypes, slightly more than 40% had het sub-genotypes, with het-low slightly exceeding het-high, and under 10% had hom sub-genotypes. In the IVF study, infertility patients of very advanced age (mean 39.7±5.7 year) in the morphological quality group deviated the most from this standard distribution, demonstrating fewer norm genotypes (41.1%) and a very high prevalence of low alleles. In contrast, the presumed fertile middle-aged patient in the ploidy group (mean age of 33.5±5.5) had higher than standard numbers of norm genotypes (62.1%) and relatively low numbers of het-low genotypes. The middle-aged infertility patients in the pregnancy rate group also had a high number of norm genotypes (61.7%) and a relatively low number of het-low patients. The young oocyte donors in the pregnancy rate group (mean age 25.0±2.9 years) had approximately half (50.3%) norm genotypes, 28.5% het-norm/low sub-genotypes and only 9.5% het-norm/high sub-genotypes. Overall, 35.2% of the oocyte donors undergoing oocyte retrieval carried a het-low FMR1 gene.

The IVF study demonstrates that low FMR1 alleles are associated with poor morphological embryo quality. The clinical pregnancy rate was higher using embryos produced from oocytes harvested from donors with a low FMR1 allele (60.3%) than donors with norm and/or high FMR1 alleles (53.5%), but this difference was not statistically significant (P=0.3767). This confirms it is difficult to detect adverse FMR1 effects in young human females and suggests such young human females have enough redundant ovarian function to counteract the adverse effects of FMR1 genotype on ovarian function. Additionally, this is the rate of clinical pregnancy using embryos selected for implantation. The rate of clinical pregnancy in comparison to attempted IVF oocyte harvesting cycles in human female with an FMR1-low allele may be substantially lower.

FMR1-related differences in IVF pregnancy rates, however, are apparent at young ages, and the differences between het-low and all other FMR1 genotypes do not change dramatically with age (see, FIG. 15). Moreover, FMRP and FMR1 mRNA are expressed during all stages of follicle development in rodents. As such, FMR1 has a direct effect on oocytes throughout a human female's reproductive life.

Due to the redundancy of ovarian reserve in young women, the IVF study did not observe a significant decrease in pregnancy rates in donor cycles when the donor has at least one low FMR1 allele. This redundancy, however, is not sufficient to maintain cumulative pregnancy chances over sequential donor IVF cycles utilizing fresh and frozen embryos. As a result, cumulative clinical pregnancy rates are expected to decline over successive IVF cycles using donor embryos from donors with low FMR1 alleles. Donor candidates with low FMR1 alleles and/or low ovarian reserve should be excluded from IVF donation to optimize cumulative pregnancy rates in successive donor IVF cycles.

Additionally, the greater likelihood of poor morphology in embryos created from oocytes harvested from women with low FMR1 alleles supports the exclusion of such women from oocyte donation programs. Because poor embryo morphology can result in poor IVF outcomes, donor candidates whose oocytes are likely to have poor morphology should be excluded from oocyte donation programs. The results of the morphology sub-part of the IVF study supports excluding human females with FMR1-low alleles from oocyte donation programs.

Many IVF programs currently test oocyte donor's FMR1 status to prevent transmission of maternal premutation range ($CGG_{n.55-200}$) and/or full mutation range ($CGG_{n>200}$) FMR1 genes. Transmission of FMR1 genes in those ranges would result in FXS and other neuro-psychiatric complications that mostly affect males. Such testing, however, is only performed after a human female already has been selected as an oocyte donor. Based on the results of the IVF study, FMR1 testing should be performed in oocyte donor candidates as a tool of primary selection as oocyte donors. Particularly, an FMR1 test should be performed on oocyte donor candidates as early as possible in the selection process and only candidates with no low FMR1 alleles should optimally be selected as oocyte donors.

Human females with the norm-low FMR1 genotype overproduce FMRP, resulting in increased in FMRP levels in such females as compared to human females with the norm FMR1 genotype. This increase may explain the varying reproductive success among women with the various FMR1 genotypes. Specifically, increased FMRP levels reduce reproductive success in human females with FMR1 low alleles. Administering an FMR1 inhibitor to a human female with one or more FMR1 low alleles may reduce that female's increased FMRP levels and, thereby, reduce the negative effects of her FMR1 low genotype on her reproductive success. As defined in U.S. Pat. No. 8,629,120, an FMR1 inhibitor is any compound or treatment that reduces expression of the FMR1 gene, including, without limitation, pharmaceutical agents, transcription factors, gene therapy and/or RNAi. Administering an FMR1 inhibitor to an oocyte donor may improve reproductive success using oocytes from that donor.

In view of the foregoing, the following methods for selecting oocyte donors are described, combined with screening methods that increase the likelihood of clinical pregnancy in IVF patients. Using FMR1 genotype data, young oocyte donor candidates can be screened for the likelihood that their oocytes will produce embryos of high morphological quality and the likelihood that use of their oocytes will result in clinical pregnancy in IVF patients.

While the foregoing written description of the invention enables one of ordinary skill to make and use what is considered presently to be the best mode thereof, those of ordinary skill will understand and appreciate the existence of variations, combinations, and equivalents of the specific exemplary embodiments thereof. The invention is not limited by the exemplary embodiments herein, but by all embodiments within the scope and spirit of the appended claims.

We claim:

1. A method of improving oocytes from an oocyte donor, comprising:
   isolating an FMR1 gene from the oocyte donor;
   measuring the number of triple CGG repeats on each allele of the isolated FMR1 gene by using an assay;
   determining that the number of triple CGG repeats on at least one of the alleles of the isolated FMR1 gene is less than 26;
   administering an FMR1 inhibitor to the oocyte donor to reduce expression of the oocyte donor's FMR1 gene when it is determined that the number of triple CGG repeats on at least one of the alleles of the isolated FMR1 gene is less than 26; and thereafter
   harvesting an oocyte from the oocyte donor.

2. The method of claim 1, further comprising:
   performing in vitro or in vivo fertilization using the harvested oocyte; and
   implanting an embryo created through said fertilization of said oocyte in a human female.

3. A method of selecting a human female oocyte donor, comprising:
   identifying a human female as an oocyte donor candidate;
   isolating an FMR1 gene from said candidate;
   measuring a number of triple CGG repeats on each allele of the isolated FMR1 gene by using an assay;
   determining that the number of CGG repeats on both of the alleles of the FMR1 gene of said candidate is more than 26; and
   selecting said candidate to be an oocyte donor after it is determined that the number of CGG repeats on both of the alleles of the FMR1 gene of said candidate is more than 26.

4. The method of claim 3, further comprising:
   harvesting an oocyte from the candidate;
   performing in vitro or in vivo fertilization using the oocyte; and
   implanting an embryo created through said fertilization of said oocyte in a human female.

5. A method of selecting an oocyte donor pool, comprising:
   identifying a plurality of oocyte donor candidates;
   isolating an FMR1 gene from each of said candidates;
   measuring a number of triple CGG repeats on a first and second allele of each isolated FMR1 gene by using an assay; and
   excluding from the oocyte donor pool any of said candidates who has an FMR1 gene with at least one allele with fewer than 26 CGG repeats.

6. The method of claim 5, wherein at least one candidate is excluded from the oocyte donor pool.

7. The method of claim 5, wherein each candidate who has an FMR1 gene with at least one allele with fewer than 26 CGG repeats is excluded from the oocyte donor pool.

8. The method of claim 5, further comprising:
   harvesting at least one oocyte from at least one oocyte donor in the donor pool;

performing in vitro or in vivo fertilization using at least one of said at least one oocytes; and implanting at least one of embryo created through said fertilization of said at least one oocyte in a human female.

9. A method of improving morphological quality of embryos resulting from fertilization of oocytes harvested from an oocyte donor, comprising:
  isolating an FMR1 gene from the oocyte donor;
  measuring the number of triple CGG repeats on each allele of the isolated FMR1 gene by using an assay;
  determining that the number of triple CGG repeats on at least one of the alleles of the isolated FMR1 gene is less than 26;
  administering an FMR1 inhibitor to the oocyte donor to reduce expression of the oocyte donor's FMR1 gene when it is determined that the number of triple CGG repeats on at least one of the alleles of the isolated FMR1 gene is less than 26; and thereafter harvesting an oocyte from the oocyte donor.

10. The method of claim 9, further comprising:
  performing in vitro or in vivo fertilization using the harvested oocyte; and
  implanting an embryo created through the fertilization of the oocyte in a human female.

11. A method of improving pregnancy rates following in vitro fertilization using oocytes harvested from an oocyte donor, comprising:
  isolating an FMR1 gene from the oocyte donor;
  measuring the number of triple CGG repeats on each allele of the isolated FMR1 gene by using an assay;
  determining that the number of triple CGG repeats on at least one of the alleles of the isolated FMR1 gene is less than 26;
  administering an FMR1 inhibitor to the oocyte donor to reduce expression of the oocyte donor's FMR1 gene when it is determined that the number of triple CGG repeats on at least one of the alleles of the isolated FMR1 gene is less than 26; and thereafter
  harvesting an oocyte from the oocyte donor.

12. The method of claim 11, further comprising:
  performing in vitro fertilization using the harvested oocyte; and
  implanting an embryo created through the fertilization of the oocyte in a human female.

* * * * *